(12) United States Patent
Babich et al.

(10) Patent No.: US 11,167,049 B2
(45) Date of Patent: *Nov. 9, 2021

(54) ORGAN PROTECTION IN PSMA-TARGETED RADIONUCLIDE THERAPY OF PROSTATE CANCER

(71) Applicant: Molecular Insight Pharmaceuticals, Inc., New York, NY (US)

(72) Inventors: John W. Babich, New York, NY (US); Shawn Hillier, Danvers, MA (US); John Joyal, Melrose, MA (US)

(73) Assignee: Molecular Insight Pharmaceuticals, Inc., New York, NY (US)

( * ) Notice: Subject to any disclaimer, the term of this patent is extended or adjusted under 35 U.S.C. 154(b) by 11 days.

This patent is subject to a terminal disclaimer.

(21) Appl. No.: 16/860,925

(22) Filed: Apr. 28, 2020

(65) Prior Publication Data

US 2020/0254120 A1  Aug. 13, 2020

Related U.S. Application Data

(63) Continuation of application No. 15/934,304, filed on Mar. 23, 2018, now Pat. No. 10,668,174, which is a continuation of application No. 14/846,252, filed on Sep. 4, 2015, now Pat. No. 9,956,305.

(60) Provisional application No. 62/047,546, filed on Sep. 8, 2014.

(51) Int. Cl.
| | | |
|---|---|---|
| *A61K 51/04* | (2006.01) | |
| *A61K 31/555* | (2006.01) | |
| *A61K 51/12* | (2006.01) | |

(52) U.S. Cl.
CPC ........ *A61K 51/0497* (2013.01); *A61K 31/555* (2013.01); *A61K 51/0461* (2013.01); *A61K 51/12* (2013.01)

(58) Field of Classification Search
CPC ....... A61K 51/04; A61K 51/12; A61K 31/555
See application file for complete search history.

(56) References Cited

U.S. PATENT DOCUMENTS

| | | | |
|---|---|---|---|
| 6,784,153 B1 | 8/2004 | Rajotte et al. | |
| 6,875,886 B2* | 4/2005 | Frangioni ............... | A61P 13/12 560/171 |
| 8,211,401 B2 | 7/2012 | Babich et al. | |
| 8,211,402 B2 | 7/2012 | Babich et al. | |
| 8,465,725 B2 | 6/2013 | Babich et al. | |
| 8,487,129 B2 | 7/2013 | Babich et al. | |
| 8,562,945 B2 | 10/2013 | Babich et al. | |
| 2008/0311037 A1 | 12/2008 | Heston et al. | |
| 2013/0034494 A1* | 2/2013 | Babich ................. | C07D 257/02 424/1.65 |
| 2014/0107042 A1 | 4/2014 | Crapo et al. | |

FOREIGN PATENT DOCUMENTS

| | | |
|---|---|---|
| JP | 2002-506079 A | 2/2002 |
| JP | 2002-515040 A | 5/2002 |
| JP | 2010-509358 A | 3/2010 |
| WO | WO 2014/110372 A1 | 7/2014 |

OTHER PUBLICATIONS

Rosenthal, et al., "Utility of capromab pendetide (ProstaScint) imaging in the management of prostate cancer," *Techniques in Urology*, vol. 7, No. pp. 27-37 (Apr. 2001).
Ross, et al., "Correlation of Primary Tumor Prostate-Specific Membrane Antigen Expression with Disease Recurrence in Prostate Cancer," *Clin. Cancer Res.*, vol. 9, No. 17, pp. 6357-6362 (Dec. 2003).
Tagawa, S.T. et al. " Phase II study of lutetium-177 labeled anti-prostate-specific membrane antigen (PSMA) monoclonal antibody J591 for metastatic castration-resistant prostate cancer," *Clin. Cancer Res.*, vol. 19n No. 18, pp. 5182-5191 (Sep. 2013).
Afshar-Oromieh, A. et al., "PET imaging with a [$^{68}$Ga]gallium-labelled PSMA ligand for the diagnosis of prostate cancer; biodistribution in humans and first evaluation of tumour lesions," Eur. J. Nucl. Med. Mol. Imaging 40 (4): 486-95 (2013).
Afshar-Oromieh, A. et al., "Comparison of PET imaging with a $^{68}$Ga-labelled PSMA ligand and $^{18}$F-choline-based PET/CT for the diagnosis of recurrent prostate cancer," Eur. J. Nucl. Med. Mol. Imaging 41 (1): Nov. 20, 2014).
Anilkumar, G. et al., Prostate-specific Membrane Antigen Association with Filamin a Modulates Its Internalization and NAALADase Activity, Cancer Res. 63: 2645-48 (2003).
Argyrou, M. et al., "Rhenium-188 Production in Hospitals, by W-188/Re-188 Generator, for Easy Use in Radionuclide Therapy," Int. J. Mol. Imaging 2013: 290750 (2013).
Barinka, C. et al., "Substrate specificity, inhibition and enzymological analysis of recombinant human glutamate carboxypeptidase II," J. Neurochem. 80: 477-487 (2002).
Barrett, J.A. et al., "First-in-Man Evaluation of 2 High-Affinity PSMA-Avid Small Molecules for Imaging Prostate Cancer," J. Nucl. Med. 54 (3): 380-7 (2013).
Eder, M. et al., "PSMA as a target for radiolabeled small molecules," Eur. J. Nucl. Med. Mol. Imaging 40 (6): 819-23 (2013).
Ghosh et al., "Effect of carbohydrate moieties on the folate hydrolysis activity of the prostate specific membrane antigen," Prostate, 57: 149-151 (2003). [Abstract].
Hillier, et al., "$^{99m}$Tc-Labeled Small-Molecule Inhibitors of Prostate-Specific Membrane Antigen for Molecular Imaging of Prostate Cancer," Cancer Res. 69 (17): 6932-40 (2009).

(Continued)

*Primary Examiner* — Michael G. Hartley
*Assistant Examiner* — Jagadishwar R Samala
(74) *Attorney, Agent, or Firm* — Foley & Lardner LLP

(57) ABSTRACT

A method of reducing radiation exposure of a non-cancerous tissue of a patient diagnosed with a cancer includes administering to the patient an agent capable of competing for binding sites on a surface of the non-cancerous tissue, provided that the administration is carried out after a waiting period that follows administration of a compound including a radionuclide to the patient, the compound having affinity for both a cancerous tissue and the non-cancerous tissue, and, further provided that the binding sites have an affinity for both the agent and the compound.

17 Claims, 6 Drawing Sheets

(56) References Cited

OTHER PUBLICATIONS

Hillier, et al., "Preclinical Evaluation of Novel Glutamate-Urea-Lysine Analogues that Target Prostate-Specific Membrane Antigen as Molecular Imaging Pharmaceuticals for Prostate Cancer," J. Nucl. Med. 54 (8): 1369-76 (2013).
Hlouchová, K. et al., "Biochemical characterization of human glutamate carboxypeptidase III," J. Neurochem. 101 (3): 682-696 (2007).
Israeli, et al., "Expression of the Prostate-specific Membrane Antigen," Cancer Research 54: 1807-1811 (1994).
Liu, H. et al., "Constitutive and Antibody-induced Internalization of Prostate-specific membrane Antigen," Cancer Res. 58: 4055-4060 (1998).
Maresca, et al., A series of halogenated heterodimeric inhibitors of prostate specific membrane antigen (PSMA) as radiolabeled probes for targeting prostate cancer, J. Med. Chem. 52 (2): 347-57 (2009). [Abstract].
Mhawech-Fauceglia, P. et al., "Prostate-specific membrane antigen (PSMA) protein expression in normal and neoplastic tissues and its sensitivity and specificity in prostate adenocarcinoma: an immunohistochemical study using mutiple tumour tissue microarray technique," Histopathology 50 (4): 472-83 (2007).
Olson, et al., Antibody-drug conjugates targeting prostate-specific membrane antigen, Front Biosci. (Landmark Ed) 19: 12-23 (2014). [Abstract].
Pangalos, et al., Isolation and Expression of Novel Human Glutamate Carboxypeptidases with N-Acetylated a-Linked Acidic Dipeptidase and Dipeptidyl Peptidase IV Activity, J. Bio. Chem. 274: 8483 (1999).
Rovenská, M. et al., Tissue expression and enzymologic characterization of human prostate specific membrane antigen and its rat and pig orthologs, Prostate 68 (2): 171-82 (2008).
Silver, et al., "Prostate-specific membrane antigen expression in normal and malignant human tissues," Clin. Cancer Res. 3(1): 81-5 (1997).
Trover, et al., "Detection and characterization of the prostate-specific membrane antigen (PSMA) in tissue extracts and body fluids," Int. J. Cancer 62: 552-558 (1995).
Tsukamoto, et al., "Enantiospecificity of Glutamate Carboxypeptidase II Inhibition," J. Med. Chem. 48 (7): 2319-24 (2005).
Vallabhajosula, S. et al., Pharmacokinetics and biodistribution of $^{111}$In- and $^{177}$Lu-labeled J591 antibody specific for prostate-specific membrane antigen: prediction of $^{90}$Y-J591 radiation dosimetry based on $^{111}$In or $^{177}$Lu?. J Nucl Med. 2005;46:634-641.J. Nucl. Med. 46: 634-41 (2005).
Wolf, P. et al., Three conformational antibodies specific for different PSMA epitopes are promising diagnostic and therapeutic tools for prostate cancer, Prostate 70: Prostate 70 (5): 562-9 (2010).
Zechmann, et al., "Radiation dosimetry and first therapy results with a 124I/131 I-labeled small molecular (MIP-1095) targeting PSMA for prostate cancer therapy," Eur. J. Nucl. Med. Mol. Imaging, vol. 41, pp. 1280-1292 (2014).
International Preliminary Report on Patentability issued in related International Patent Application No. PCT/US2015/048651, dated Mar. 23, 2017.
International Search Report and Written Opinion issued in corresponding application No. PCT/US2015/048651 dated Jan. 29, 2016.
Kularatne, et al., "Prostate-Specific Membrane Antigen Targeted Imaging and Therapy of Prostate Cancer Using a PSMA Inhibitor as a Homing Ligand," Mol. Pharmaceutics, vol. 6, No. 3, pp. 780-789 (Apr. 2009).
Kratochwil, et al., "PMPA for Nephroprotection in PSMA-Targeted Radionuclide Therapy of Prostate Cancer," J. Nucl. Med., vol. 56, pp. 293-298 (2015).
Hillier et al., "$^{123}$I-MIP-1072, a Small-Molecule Inhibitor of Prostate-Specific Membrane Antigen, Is Effective at Monitoring Tumor Response to Taxane Therapy," J. Nucl. Med., vol. 52, pp. 1087-1093 (2011).
Office Communication issued in co-pending European Patent Application No. 15840011.9, dated Jun. 18, 2019.
Office Action issued in co-pending Japanese Patent Application No. 2017-512946, dated Jul. 2, 2019.
She, et al., "2-MPPA, a Selective Inhibitor of PSMA, Delays Prostate Cancer Growth and Attenuates Taxol-Induced Neuropathy in Mice," Journ. of Clinical Oncology, vol. 23, No. 16, Abstract No. 8054, 3 pages (2005).

* cited by examiner

FIGS. 3A-3B
A
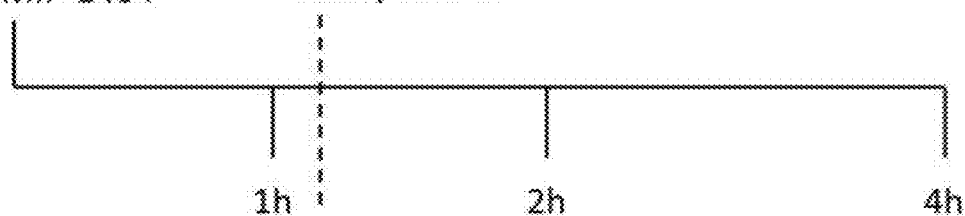
B
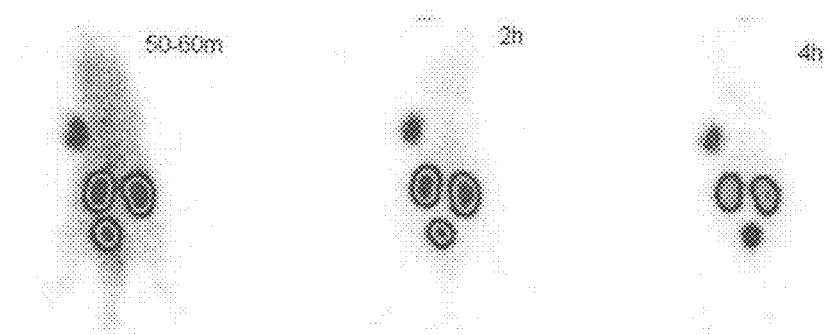
Control.
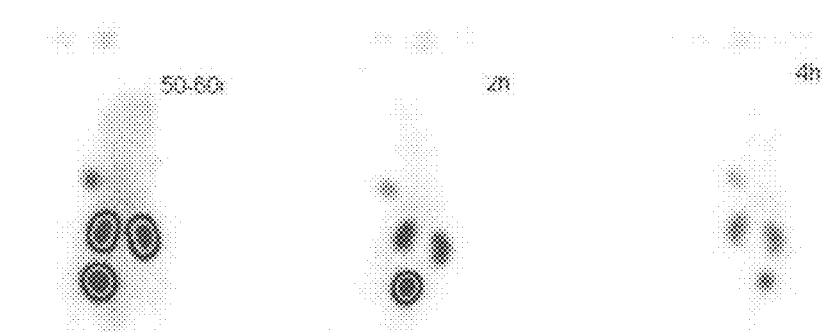
50 mg/kg:

ORGAN PROTECTION IN PSMA-TARGETED RADIONUCLIDE THERAPY OF PROSTATE CANCER

CROSS REFERENCE TO RELATED APPLICATIONS

This application is a continuation of U.S. patent application Ser. No. 15/934,304, filed on Mar. 23, 2018, which is a continuation of U.S. patent application Ser. No. 14/846,252, filed on Sep. 4, 2015, now U.S. Pat. No. 9,956,305, which claims priority from U.S. Provisional Patent Application No. 62/047,546, filed on Sep. 8, 2014. The contents of these applications are incorporated herein by reference in their entireties for any and all purposes.

FIELD

The present technology is generally related to radionuclide therapy. More particularly, it is related to preventing or minimizing ancillary radiation damage of non-target, normal tissues by radionuclides during radionuclide therapy for cancerous tissue.

BACKGROUND

The cell surface peptidase, prostate-specific membrane antigen (PSMA) demonstrates intense overexpression in the majority of both primary and metastatic prostate cancers (PCa) and is expressed on the neovasculature of the majority of solid tumors including bladder, colon, liver, lung, renal, glioblastoma multiforme and melanoma (28). This along with a positive correlation of PSMA with traditional adverse prognostic factors aroused growing interest in evaluation of this target.[1-3] Initially, antibodies (mAB) targeting PSMA have been used for PCa imaging and therapeutic approaches. The $^{111}$In labeled mAB capromab pendetide (ProstaScint, EUSA Pharma, Langhorne, Pa.) was approved in the USA in 1996. However, because the mAB, 7E11 targeted the intracellular domain of PSMA, its diagnostic value was rather limited.[4] Another monoclonal PSMA antibody, J591 targets the extracellular domain of PSMA, but like most complete mABs it presents with a slow tumor accumulation and a long circulation time in blood. Thus, diagnostic mAB-tracers require prolonged imaging—even days after injection.[5] Transferred to radionuclide therapy mABs commonly translate into an unfavorable dosimetry with pronounced hematotoxicity.[6] Recently, the development of the Glu-urea-based high affinity small molecule PSMA inhibitors MIP1072 and MIP1095, either labeled with $^{123}$I for imaging or $^{131}$I for targeted radionuclide therapy, rendered rapid tumor uptake possible.[7-9] Since PSMA is internalized through clathrin-coated pits[27] either spontaneously or after binding of an antibody or an inhibitor, it is also an excellent target for endoradiotherapy. In this respect, the accumulation of the tracer in normal tissues has to be considered to prevent or diminish the extend of side effects, particularly in normal tissues that express low levels of PSMA including the proximal renal tubules of the kidney, salivary glands, and the brush-border epithelium of the small intestines.[28]

In a positron emission tomography (PET)-based dosimetry study of $^{124}$I-MIP1095, doses of up to 300 Gy in lymph node and bone metastases of castration refractory prostate cancer (CRPCa) were calculated. The organs with the highest off-target radiation doses were salivary glands (3.8 mSv/MBq), liver (1.7 mSv/MBq) and kidneys (1.4 mSv/MBq), while red marrow was 0.37 mSv/MBq.[10] Therefore, kidneys may be the limiting factor for the maximum activity that can cumulatively be administered safely. However, improving kidney uptake without losing tumor dose is a real challenge because PSMA is physiologically expressed in the kidney tubules.[1] The pharmacokinetics of MIP-1072 and MIP-1095 in animals have already been evaluated in detail.[7] The authors reported a similar accumulation of both compounds in PSMA-expressing LNCaP xenografts but with very different pharmacokinetic profiles. MIP-1072 clears rapidly from target (tumor) and non-target (normal) tissues. In contrast, MIP-1095 presents a longer biological half-life in tumor but not in kidneys, which corresponds to a higher fraction of ligand induced receptor internalization and retention in tumor cells.

For the development of Glu-Urea based PSMA ligands, the structurally unrelated PSMA inhibitor 2-(phosphonomethyl)pentanedioic acid (PMPA) is commonly used as a competitor in blocking studies to demonstrate the specific binding of the molecule of interest, PSMA. In this respect simultaneous coinjection of 50 mg/kg PMPA resulted in a complete blocking of radiolabeled-MIP-1095 to binding sites in tumor and kidneys.[7] The present disclosure describes a surprising discovery involving selective displacement by blocking agents of radionuclides from non-target, normal tissue and organs while retaining radionuclide at target, cancerous tissue sites through non-simultaneous administration methods.

SUMMARY

Disclosed herein, in one aspect, are methods of Aing radiation exposure of a non-cancerous tissue of a patient diagnosed with a cancer, the methods comprising administering to the patient an agent capable of competing for binding sites on a surface of the non-cancerous tissue, provided that the administration is carried out after a waiting period that follows administration of a compound comprising a radionuclide to the patient, the compound having affinity for both a cancerous tissue and the non-cancerous tissue, and, further provided that the binding sites have an affinity for both the agent and the compound.

In another aspect, disclosed herein are methods of reducing radiation exposure of a non-cancerous tissue of a patient diagnosed with a cancer, the methods comprising administering to the patient an effective amount of an agent, allowing a waiting period to pass and administering an effective amount of a compound comprising a radionuclide, the agent being capable of competing with the compound for binding sites on a surface of the non-cancerous tissue.

In another aspect, disclosed herein are methods of radionuclide therapy for treating prostate cancer in a subject, the methods comprising administering a compound comprising a radionuclide to the subject, allowing a waiting period of about 10 hours to about 36 hours following the administration of the compound, and then administering an agent to the subject, wherein the agent comprises a recognition moiety for binding sites of the compound in non-cancerous tissue, wherein the binding sites have an affinity for both the agent and the compound.

In another aspect, disclosed herein are methods of radionuclide therapy for treating prostate cancer in a subject, the methods comprising administering an agent to the subject, allowing a waiting period of about 10 hours to about 36 hours following the administration of the agent, and then administering a compound comprising a radionuclide to the subject, wherein the agent comprises a recognition moiety for binding sites of the compound in non-cancerous tissue, wherein the binding sites have an affinity for both the agent and the compound.

In another aspect, disclosed herein are methods of reducing ancillary radiation damage to non-cancerous tissue during radiotherapy for cancer treatment in a subject harboring cancerous tissue, the methods comprising administering a compound comprising a radionuclide to the subject, allowing a waiting period, and administering an agent to the subject after completion of the waiting period, wherein the agent is capable of reducing a concentration of the compound in the non-cancerous tissue to a greater extent than a concentration of the compound in the cancerous tissue.

In another aspect, disclosed herein are methods of reducing ancillary radiation damage to non-cancerous tissue during radiotherapy for cancer treatment in a subject harboring cancerous tissue, the methods comprising administering an agent to the subject, allowing a waiting period, and administering a compound comprising a radionuclide to the subject after completion of the waiting period, wherein the agent is capable of reducing a concentration of the compound in the non-cancerous tissue to a greater extent than a concentration of the compound in the cancerous tissue.

In another aspect, disclosed herein are therapeutic radionuclide regimens for treating cancerous tissue in a subject, the regimens comprising administering a compound comprising a radionuclide to a subject harboring a cancerous tissue, and administering an agent to the subject after allowing a waiting period to pass, in which the agent is configured to reduce radionuclide concentration in non-cancerous tissue relative to a concentration of radionuclide in the non-cancerous tissue prior to administration of the agent.

In another aspect, disclosed herein are therapeutic radionuclide regimens for treating cancerous tissue in a subject, the regimens comprising administering an agent to a subject harboring a cancerous tissue, and administering a compound comprising a radionuclide to the subject after allowing a waiting period to pass, in which the agent is configured to reduce radionuclide concentration in non-cancerous tissue relative to a concentration of radionuclide in the cancerous tissue.

In another aspect, disclosed herein are therapeutic radionuclide regimens for treating cancerous tissue in a subject, the regimens comprising administering a compound comprising a radionuclide to a subject harboring a cancerous tissue, and administering an agent to the subject after allowing a waiting period to pass, in which the agent is configured to compete with the compound for binding sites on a surface of non-cancerous tissue.

In another aspect, disclosed herein are therapeutic radionuclide regimens for treating cancerous tissue in a subject, the regimens comprising administering an agent to a subject harboring a cancerous tissue, and administering a compound comprising a radionuclide to the subject after allowing a waiting period to pass, in which the agent is configured to compete with the compound for binding sites on a surface of non-cancerous tissue.

In another aspect, disclosed herein are treatment protocols for a subject diagnosed with cancer, the protocols comprising: administering a compound comprising a radionuclide to the subject, allowing a waiting period to pass, successively administering to the subject multiple, low-concentration doses of an agent capable of reducing a radionuclide concentration in non-cancerous tissue in the subject to a greater extent than a radionuclide concentration in cancerous tissue in the subject, observing between successive doses of the agent a concentration change of the compound in non-cancerous tissue until a desired non-cancerous tissue concentration of the radionuclide is obtained, and discontinuing administration of the agent.

In another aspect, disclosed herein are kits comprising:
a) a compound comprising a radionuclide;
b) a blocking agent for reducing ancillary radiation damage to non-cancerous tissue, wherein both the compound and the agent comprise a recognition moiety for prostate specific membrane antigen.

In another aspect, disclosed herein are treatment protocols for a subject diagnosed with cancer, the protocols comprising:
a) administering to the subject a compound comprising a radionuclide,
b) allowing a waiting period to pass,
c) administering to the subject an agent in an amount sufficient to cause a displacement of radionuclide in non-cancerous tissue and retention of radionuclide in cancerous tissue.

In another aspect, disclosed herein are treatment protocols for a subject diagnosed with cancer, the protocols comprising:
a) administering to the subject an agent,
b) allowing a waiting period to pass,
c) administering to the subject a compound comprising a radionuclide, wherein the compound is administered in an amount sufficient to cause a displacement of the agent in cancerous tissue.

In another aspect, disclosed herein are methods of reducing exposure of one's non-cancerous tissue to radiation, the methods comprising receiving an agent comprising a recognition moiety, wherein the recognition moiety is for a binding site of a compound, and the compound comprises a radionuclide, provided that the receiving step is carried out after a waiting period that follows a prior step of receiving the compound comprising the radionuclide.

In another aspect, disclosed herein are methods of reducing exposure of one's non-cancerous tissue to radiation, the methods comprising receiving a compound comprising a radionuclide, provided that the receiving step is carried out after a waiting period that follows a prior step of receiving an agent comprising a recognition moiety, wherein the recognition moiety is for a binding site of the compound.

BRIEF DESCRIPTION OF THE DRAWINGS

FIG. 3A is a chart showing the experimental setup with the first image at 1 hour post-injection of the Compound comprising a radionuclide, $^{99m}$Tc MIP-1404. Immediately after scintigraphy saline (control group) or 50 mg/kg PMPA were administered, additional imaging was conducted at the indicated time periods post injection. FIG. 3B shows scintigraphic images of a control and a PMPA treated animal, according to the examples.

DETAILED DESCRIPTION

Figure 1A:
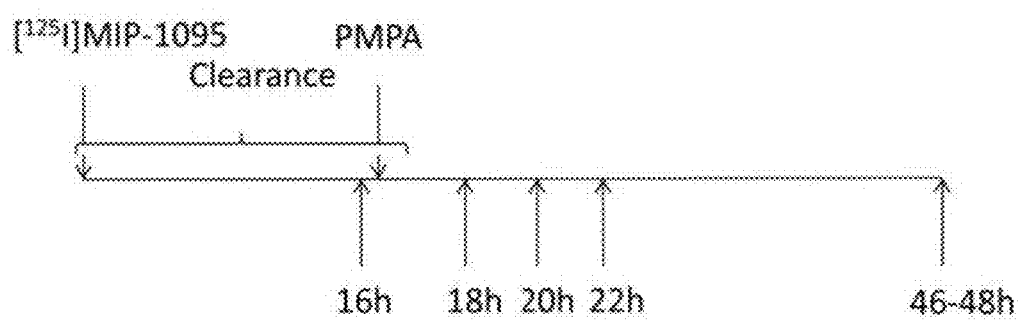
FIG. 1A is a chart illustrating the experimental setup with the first image at 16 hours post-injection of the compound comprising a radionuclide, [$^{125}$I] MIP-1095. Immediately after scintigraphy, saline (control group) or different doses of the blocking agent, PMPA, were given and additional imaging was conducted at the indicated time periods post injection.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

It has been found that during radionuclide therapy for cancerous tissue in a subject, ancillary radiation damage of normal tissue in a subject may be reduced by administration of a blocking agent to the subject. In some embodiments, the blocking agent is administered to the subject after an induction period for an administered radionuclide, i.e., a time period during which an administered radionuclide-containing compound is allowed to localize in various tissues. In other embodiments, the blocking agent is administered to the subject prior to the administration of a radionuclide. The radionuclide-containing compounds described herein have a recognition moiety for a cancerous (i.e., tumor) tissue For example, in some embodiments, the compound may have a recognition moiety for prostate specific membrane antigen (PSMA), and the compound may contain a radionuclide as part of the compound, or the compound may have a chelation group bound to a radionuclide. In one embodiment, the compound is a Glu-Urea-based PSMA ligand. The blocking agents are materials which are not radiolabeled and will displace the radionuclide-containing compound from normal (i.e., non-cancerous or non-tumor) tissue, while not have any effect, or at least a lesser effect on displacement of the radionuclide-containing compound from the cancerous tissue. For example, in some embodiments, the blocking agent has a recognition moiety for prostate specific membrane antigen. In further embodiments, the binding sites on a surface tissue have an affinity for both the compound and the blocking agent. In some embodiments, the blocking agent is a compound without a radiolabel or a cold compound.

In one aspect, a method is provided for reducing radiation exposure of a tissue of a patient diagnosed with a cancer, which tissue is substantially free of tumor tissue. In some embodiments, the method includes administering to the patient an agent capable of competing for binding sites on a surface of the tissue, provided that the administration is carried out after a waiting period that follows administration of compound having a radionuclide to the patient, and, further provided that the binding sites have an affinity for both the agent and the radionuclide. In other embodiments, the method includes administering to the patient a compound having a radionuclide, provided that the administration is carried out after a waiting period that follows administration of an agent to the patient, the agent being capable of competing for binding sites on a surface of the non-cancerous tissue, and the compound having affinity for both a cancerous tissue and the non-cancerous tissue, and, further provided that the binding sites have an affinity for both the agent and the compound.

In some embodiments disclosed herein are methods of reducing radiation exposure of a non-cancerous tissue of a patient diagnosed with a cancer, the method including administering to the patient an agent capable of competing for binding sites on a surface of the non-cancerous tissue, provided that the administration is carried out after a waiting period that follows administration of a compound comprising a radionuclide to the patient, the compound having affinity for both a cancerous tissue and the non-cancerous tissue, and, further provided that the binding sites have an affinity for both the agent and the compound. In some embodiments, the agent displaces bound radionuclide from the binding sites thereby reducing the exposure of the non-cancerous tissue. In some embodiments, the agent does not comprise a radionuclide. In some embodiments, the agent comprises the compound without the radionuclide.

In some embodiments disclosed herein are methods of reducing radiation exposure of a non-cancerous tissue of a patient diagnosed with a cancer, the method including administering to the patient an effective amount of a compound comprising a radionuclide, allowing a waiting period to pass, and administering an effective amount of an agent capable of competing with the compound for binding sites on a surface of the non-cancerous tissue. In some embodiments, the compound exhibits an affinity for both a cancerous tissue and the non-cancerous tissue. In some embodiments, the binding sites have an affinity for both the agent and the compound. In some embodiments, the agent displaces bound radionuclide from the binding sites thereby reducing the exposure of the non-cancerous tissue. In some embodiments, the agent does not comprise a radionuclide. In some embodiments, the agent comprises the compound without the radionuclide.

In some embodiments disclosed herein are methods of reducing radiation exposure of a non-cancerous tissue of a patient diagnosed with a cancer, the methods comprising administering to the patient an effective amount of an agent, allowing a waiting period to pass and administering an effective amount of a compound comprising a radionuclide, the agent being capable of competing with the compound for binding sites on a surface of the non-cancerous tissue. In some embodiments, the compound exhibits an affinity for both a cancerous tissue and the non-cancerous tissue. In some embodiments, the binding sites have an affinity for both the agent and the compound. In some embodiments, the agent does not comprise a radionuclide. In some embodiments, the agent comprises the compound without the radionuclide.

In another aspect, a method of radionuclide therapy is provided for treating cancerous tissue in a subject. The method includes administering a compound having a radionuclide, i.e., a radionuclide-containing compound, to the subject harboring the cancerous tissue, allowing a waiting period to pass, and administering an agent to the subject. The agent is configured to reduce radionuclide concentration in normal or non-cancerous tissue. In some embodiments, the cancerous tissue is prostate cancer or metastatic prostate cancer. The non-cancerous tissue may be wide range of normal bodily tissues, including, but not limited to kidney tissue, salivary gland tissue, lacrimal gland tissue, parotid gland tissue, and small intestine tissue.

In some embodiments disclosed herein are methods of radionuclide therapy for treating prostate cancer in a subject, the method comprising administering a compound comprising a radionuclide to the subject, allowing a waiting period of about 10 hours to about 36 hours following the administration of the compound, and then administering an agent to the subject, wherein the agent comprises a recognition moiety for binding sites of the compound in non-cancerous tissue, wherein the binding sites have an affinity for both the agent and the compound.

In another aspect, a method of radionuclide therapy is provided for treating cancerous tissue in a subject. The method includes administering an agent to the subject harboring the cancerous tissue, allowing a waiting period to pass, and administering to the subject a compound having a radionuclide, i.e., a radionuclide-containing compound. The agent is configured to reduce radionuclide concentration in normal or non-cancerous tissue. In some embodiments, the cancerous tissue is prostate cancer or metastatic prostate cancer. The non-cancerous tissue may be wide range of normal bodily tissues, including, but not limited to kidney tissue, salivary gland tissue, lacrimal gland tissue, parotid gland tissue, and small intestine tissue.

In some embodiments disclosed herein are methods of radionuclide therapy for treating prostate cancer in a subject, the methods comprising administering an agent to the subject, allowing a waiting period of about 10 hours to about 36 hours following the administration of the agent, and then administering a compound comprising a radionuclide to the subject, wherein the agent comprises a recognition moiety for binding sites of the compound in non-cancerous tissue, wherein the binding sites have an affinity for both the agent and the compound.

In another aspect, a method of reducing ancillary radiation organ damage during radiotherapy for cancer treatment of a subject is provided. In some embodiments, the method includes administering a compound including a radionuclide, as defined above, to the subject, allowing an induction period, and administering an agent to the subject after completion of the induction period. In other embodiments, the method includes administering an agent to the subject, allowing an induction period, and administering to the subject a compound including a radionuclide, as defined above, after completion of the induction period. The agent is configured to reduce radionuclide concentration in non-cancerous tissue.

In another aspect, a method of reducing ancillary radiation damage to non-cancerous tissue during radiotherapy for cancer treatment in a subject harboring cancerous tissue is provided. In some embodiments, the method includes administering a compound comprising a radionuclide to the subject, allowing a waiting period, and administering an agent to the subject after completion of the waiting period, wherein the agent is capable of reducing a radionuclide concentration in the non-cancerous tissue to a greater extent that a radionuclide concentration in the cancerous tissue. In other embodiments, the method includes administering an agent to the subject, allowing a waiting period, and administering to the subject a compound comprising a radionuclide after completion of the waiting period, wherein the agent is capable of reducing a radionuclide concentration in the non-cancerous tissue to a greater extent that a radionuclide concentration in the cancerous tissue.

In another aspect, a treatment protocol for a subject diagnosed with cancer is provided. The protocol includes administering a compound having a radionuclide to the subject, allowing a waiting period to pass, successively administering to the subject multiple, low-concentration doses of an agent capable of reducing a radionuclide concentration in non-cancerous tissue in the subject to a greater extent that a radionuclide concentration in cancerous tissue in the subject, observing between successive doses of the agent a concentration change of the compound in non-cancerous tissue until a desired non-cancerous tissue concentration of the radionuclide is obtained, and discontinuing administration of the agent. Accordingly, the treatment protocol is essentially a titration of the compound from the body of the subject. Low-concentration doses are used such that large amounts of the compound are not displaced from tissue to which it is bound as a result of any single administered dose. Rather, the displacement of the compound from non-cancerous tissue is approached slowly such that higher radionuclide concentrations may be maintained in target, or cancerous tissue. As used herein, a low concentration dose concentration may be from about 0.01 mg/kg to about 10 mg/kg. In other embodiments, the low concentration dose is from about 0.2 mg/kg to about 10 mg/kg. In some embodiments, the low concentration dose is from about 0.01 mg/kg to about 5 mg/kg. In some embodiments, the low concentration dose is from about 0.01 mg/kg to about 1 mg/kg. In some embodiments, the low concentration dose is from about 0.01 mg/kg to about 0.5 mg/kg. In some embodiments, the low concentration dose is from about 0.01 mg/kg to about 0.1 mg/kg. In some embodiments, the low concentration dose is from about 0.2 mg/kg to about 5 mg/kg.

In another aspect, a method of radionuclide therapy for treating prostate cancer in a subject is provided. The method includes administering a compound including a radionuclide, as defined above, to the subject, allowing a waiting period of about 10 hours to about 36 hours, and administering a binding agent to the subject. In some embodiments, the binding agent is selected from cold MIP-1555, cold MIP-1519, cold MIP-1545, cold MIP-1427, cold MIP-1428, cold MIP-1379, cold MIP-1072, cold MIP-1095, cold MIP-1558, cold MIP-1405, and cold MIP-1404.

In another aspect, a method of radionuclide therapy for treating prostate cancer in a subject is provided. In some embodiments, the method includes administering a compound including a radionuclide, as defined above, to the subject, allowing a waiting period of about 10 hours to about 36 hours, and administering a binding agent to the subject. In other embodiments, the method includes administering a binding agent to the subject, allowing a waiting period of about 10 hours to about 36 hours, and administering to the subject a compound including a radionuclide, as defined above. In some embodiments, the binding agent is selected from cold MIP-1555, cold MIP-1519, cold MIP-1545, cold MIP-1427, cold MIP-1428, cold MIP-1379, cold MIP-1072, cold MIP-1095, cold MIP-1558, cold MIP-1405, and cold MIP-1404.

In another aspect, a method of radionuclide therapy for treating prostate cancer in a subject is provided. In some embodiments, the method includes administering a compound including a radionuclide, as defined above, to the subject, allowing a waiting period of about 10 hours to about 36 hours, and administering 2-(phosphonomethyl)pentanedioic acid or 2-(3-mercaptopropyl)pentanedioic acid (2-MPPA) to the subject. In other embodiments, the method includes administering 2-(phosphonomethyl)pentanedioic acid or 2-(3-mercaptopropyl)pentanedioic acid (2-MPPA) to the subject, allowing a waiting period of about 10 hours to about 36 hours, and administering a compound including a radionuclide, as defined above, to the subject.

In another aspect, a method of radionuclide therapy for treating prostate cancer in a subject is provided. In some embodiments, the method includes administering a compound having a radionuclide to the subject, allowing a waiting period of about 10 hours to about 36 hours following the administration of the compound, and then administering 2-(phosphonomethyl)pentanedioic acid or 2-MPPA to the subject. In other embodiments, the method includes administering 2-(phosphonomethyl)pentanedioic acid or 2-MPPA to the subject, allowing a waiting period of about 10 hours to about 36 hours following the administration of the compound, and then administering a compound having a radionuclide to the subject.

In another aspect, a treatment protocol for a subject diagnosed with cancer is provided. The protocol includes (a) administering to the subject a compound including a radionuclide, (b) allowing a waiting period to pass, (c) administering to the subject an agent in an amount sufficient to cause a displacement of radionuclide in non-cancerous tissue and retention of radionuclide in cancerous tissue. In some embodiments, the protocol includes administering to the subject the agent at a frequency sufficient to maintain displacement of the radionuclide from the non-cancerous tissue. In other embodiments, the protocol includes administering additional compound, followed by additional agent. In some embodiments, at least one of steps (a) and (c) are repeated at periodic intervals. In some embodiments, steps (a), (b), and (c) are repeated. In some embodiments, step (c) is repeated. In some embodiments, the displacement is at kidney, salivary glands, parotid glands, lacrimal glands, small intestines, or combination thereof. In some embodiments, the protocol further includes (d) monitoring treatment by imaging using scintigraphy, SPECT, or PET. In further embodiments, the protocol further includes determining that a significant amount of radionuclide activity remains in the non-cancerous tissue by the monitoring, and administering additional agent.

In another aspect, a treatment protocol for a subject diagnosed with cancer is provided. The protocol includes (a) administering an agent to the subject, (b) allowing a waiting period to pass, (c) administering to the subject a compound including a radionuclide, wherein the compound is administered in an amount sufficient to cause a displacement of the agent in cancerous tissue. In some embodiments, the protocol includes administering to the subject the compound at a frequency sufficient to maintain displacement of the agent from the cancerous tissue. In other embodiments, the protocol includes administering additional agent, followed by additional compound. In some embodiments, at least one of steps (a) and (c) are repeated at periodic intervals. In some embodiments, steps (a), (b), and (c) are repeated. In some embodiments, step (c) is repeated. In some embodiments, the displacement is at kidney, salivary glands, parotid glands, lacrimal glands, small intestines, or combination thereof. In some embodiments, the protocol further includes (d) monitoring treatment by imaging using scintigraphy, SPECT, or PET. In further embodiments, the protocol further includes determining that there is insufficient radionuclide activity in the cancerous tissue by the monitoring, and administering additional compound. In other embodiments, the protocol further includes determining that a significant amount of radionuclide activity is in the non-cancerous tissue by the monitoring, and administering additional agent.

In another aspect, a method of reducing exposure of one's tissue to radiation is provided, which tissue is substantially free of tumor tissue. In some embodiments, the methods include receiving an agent capable of competing for binding sites on a surface of the tissue, provided that the receiving step is carried out after a waiting period that follows a prior step of receiving a compound comprising a radionuclide, and further provided that the binding sites have an affinity for both the agent and the radionuclide. In other embodiments, the methods include receiving a compound comprising a radionuclide, provided that the receiving step is carried out after a waiting period that follows a prior step of receiving an agent capable of competing for binding sites on a surface of the tissue, and further provided that the binding sites have an affinity for both the agent and the radionuclide. In some embodiments, tissue which is substantially free of tumor tissue has less than 10% tumor tissue. In some embodiments, tissue which is substantially free of tumor tissue has less than 7% tumor tissue. In some embodiments, tissue which is substantially free of tumor tissue has less than 5% tumor tissue. In some embodiments, tissue which is substantially free of tumor tissue has less than 3% tumor tissue. In some embodiments, tissue which is substantially free of tumor tissue has less than 2% tumor tissue. In some embodiments, tissue which is substantially free of tumor tissue has less than 1% tumor tissue.

In another aspect, methods of reducing exposure of one's non-cancerous tissue to radiation are provided. In some embodiments, the methods include receiving an agent comprising a recognition moiety, wherein the recognition moiety is for a binding site of a compound, and the compound comprises a radionuclide, provided that the receiving step is carried out after a waiting period that follows a prior step of receiving the compound comprising the radionuclide. In other embodiments, the methods include receiving a compound comprising a radionuclide, provided that the receiving step is carried out after a waiting period that follows a prior step of receiving an agent comprising a recognition moiety, wherein the recognition moiety is for a binding site of the compound. In some embodiments, one's non-cancerous tissue includes non-cancerous kidney tissue. In some embodiments, one's non-cancerous tissue includes non-cancerous salivary gland tissue, parotid gland tissue, or lacrimal gland tissue.

In another aspect, a kit is provided. The kit may include a compound having a radionuclide; a blocking agent for reducing ancillary radiation damage to non-cancerous tissue, wherein both the compound and the agent have a recognition moiety for prostate specific membrane antigen. The kits may also include instructions for use.

In another aspect, a therapeutic radionuclide regimen for treating cancerous tissue in a subject is provided. In some embodiments, the regimen includes administering a compound comprising a radionuclide to a subject harboring a cancerous tissue, and administering an agent to the subject after allowing a waiting period to pass, in which the agent is configured to reduce radionuclide concentration in non-cancerous tissue relative to a concentration of radionuclide in the non-cancerous tissue prior to administration of the agent. In other embodiments, the regimen includes administering an agent to a subject harboring a cancerous tissue, and administering a compound comprising a radionuclide to the subject after allowing a waiting period to pass, in which the agent is configured to reduce radionuclide concentration in non-cancerous tissue relative to a concentration of radionuclide in the cancerous tissue. In some embodiments, the regimen includes administering a compound comprising a radionuclide to a subject harboring a cancerous tissue, and administering an agent to the subject after allowing a waiting period to pass, in which the agent is configured to compete with the compound for binding sites on a surface of non-cancerous tissue. In some embodiments, the regimen includes administering an agent to a subject harboring a cancerous tissue, and administering a compound comprising a radionuclide to the subject after allowing a waiting period to pass, in which the agent is configured to compete with the compound for binding sites on a surface of non-cancerous tissue.

In any of the above methods or treatment protocols or regimens or kits, and unless otherwise specified, the cancer or cancerous tissue may be prostate cancer. In any of the above methods or treatment protocols or regimens or kits, and unless otherwise specified, the cancerous tissue may be prostate cancer or metastatic prostate cancer. In any of the above methods or treatment protocols or regimens or kits, and unless otherwise specified, the cancerous tissue or a neovasculature associated with a solid cancer expresses Prostate Specific Membrane Antigen (PSMA). In any of the above methods or treatment protocols or regimens or kits, unless otherwise specified, the non-cancerous tissue may include, but is not limited to, kidney tissue, salivary gland tissue, lacrimal gland tissue, parotid gland tissue, or small intestines. In some embodiments, the methods or treatment protocols or regimens or kits serve to reduce or prevent radiation-induced damage to non-cancerous tissue including for example kidney damage or development of xerostomia.

In some embodiments of any of the above methods or treatment protocols or regimens or kits, the binding site is PSMA.

In any of the above methods or treatment protocols or regimens or kits, and unless otherwise specified, the radionuclide may be, but is not limited to, a radioactive isotope of Ga, I, Y, Lu, Bi, Ac, Re, In, Th, or Tc. Illustrative radionuclides include, but are not limited to, $^{186}$Re, $^{188}$Re, $^{99}$Tc, $^{68}$Ga, $^{111}$In, $^{90}$Y, $^{177}$Lu, $^{213}$Bi, $^{225}$Ac, $^{228}$Th, $^{229}$Th, $^{229m}$Th, $^{230}$Th, $^{231}$Th, $^{232}$Th, $^{233}$Th, $^{234}$Th, $^{123}$I, $^{124}$I, $^{125}$I, or $^{131}$I.

In any of the above methods or treatment protocols or regimens or kits, and unless otherwise specified, the compound including the radionuclide may have a recognition moiety for a particular cancer, cancerous tissue, or other tissue-related material associated with a particular cancer. For example, where the cancer is prostate cancer, the compound may include a recognition moiety for prostate specific membrane antigen, including for example, Glu-Urea based PSMA ligands. Such compounds include those described in U.S. Pat. Nos. 8,211,401; 8,211,402; 8,465,725; 8,487,129; and 8,562,945; and in PCT/US2014/011047. In some embodiments, the compound is MIP-1555, MIP-1519, MIP-1545, MIP-1427, MIP-1428, MIP-1379, MIP-1072, MIP-1095, MIP-1558, MIP-1405, or MIP-1404:

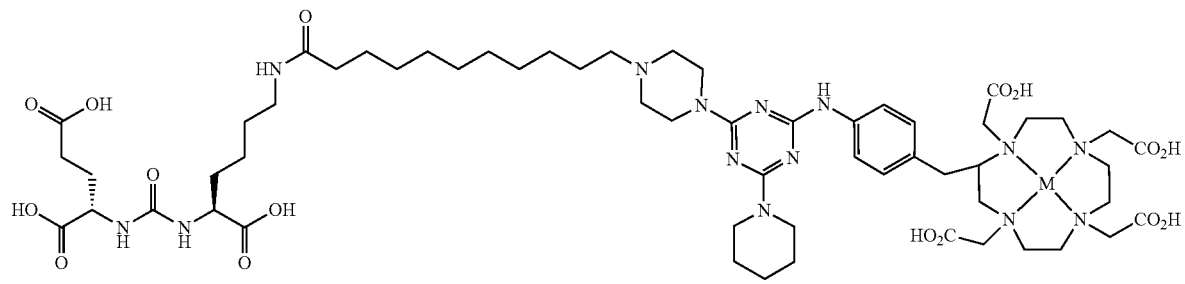

MIP-1555

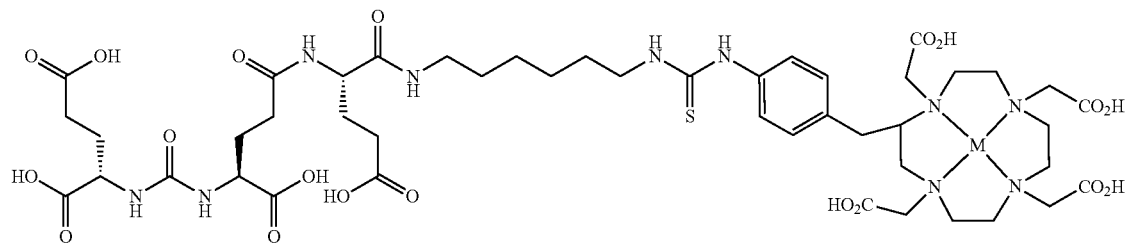

MIP-1519

-continued
MIP-1545
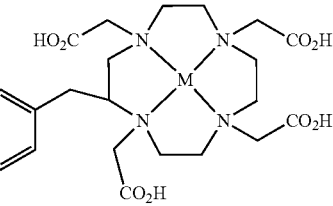
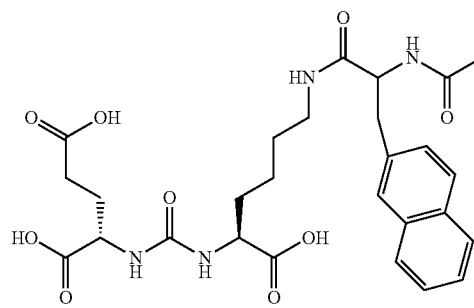
MIP-1558
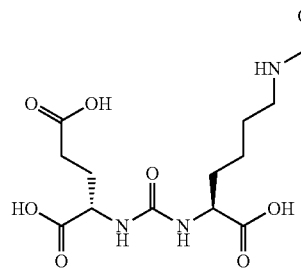
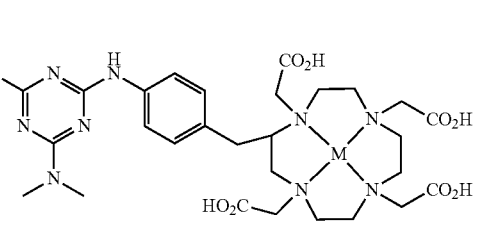
MIP-1072
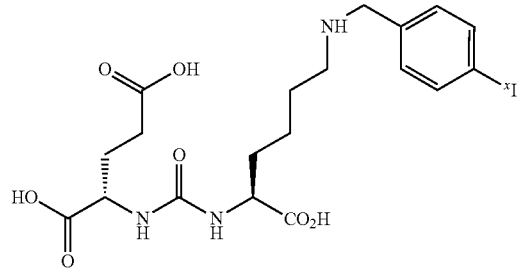
MIP-1095
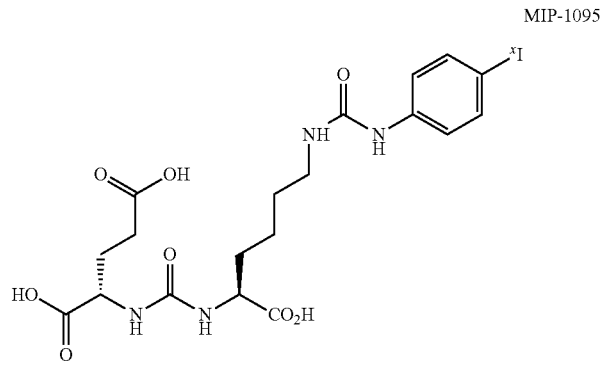
MIP-1427
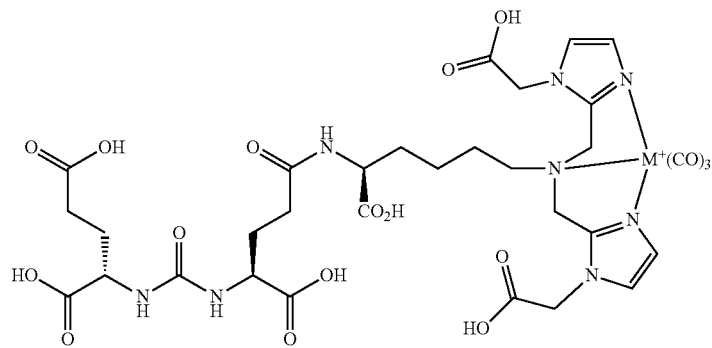

-continued
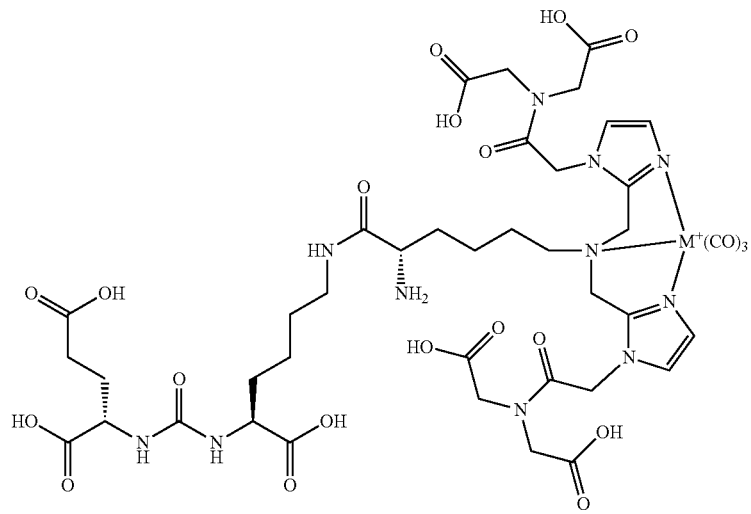
MIP-1428
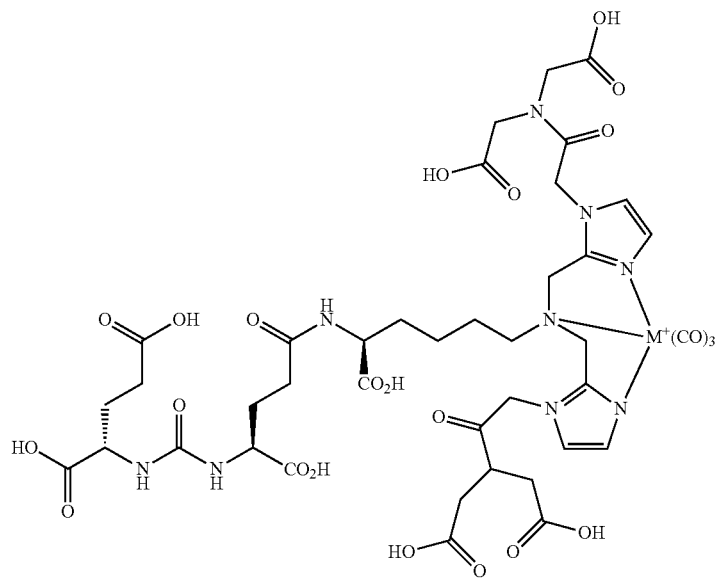
MIP-1404
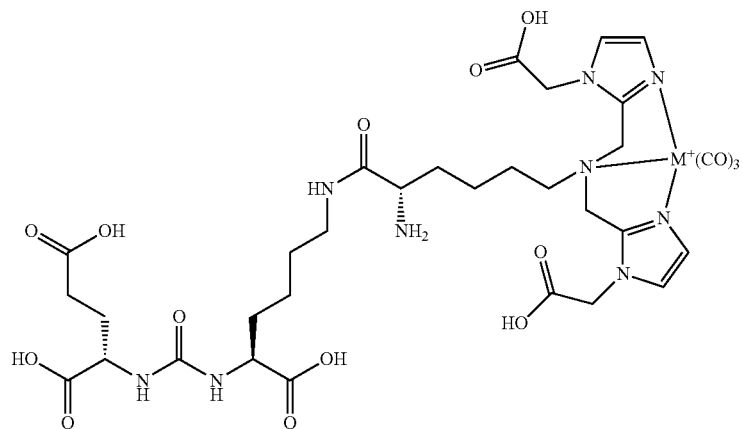
MIP-1405

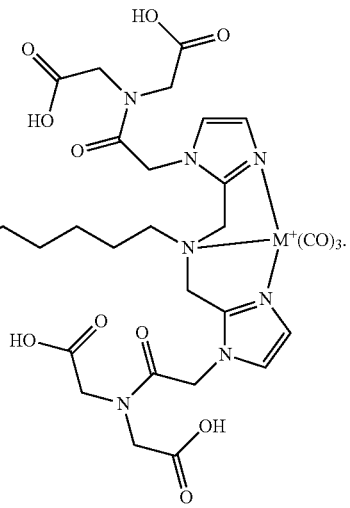

MIP-1379

In the structural representations of MIP-1072 and MIP-1095, *I refers to a radionuclide of iodine. In the structural representations of MIP-1558, MIP-1555, MIP-1545, MIP-1519, MIP-1427, MIP-1428, MIP-1405, MIP-1379, MIP-1405, and MIP-1404, M is a metal that is a radionuclide. In some embodiments, the compound is a Glu-urea-based PSMA ligand. In any of the above methods or treatment protocols or regimens, unless otherwise specified, the compound may be administered to the subject from about 0.2 mg/kg to about 100 mg/kg. In some embodiments, the amount is from about 1 mg/kg to about 50 mg/kg. In yet other embodiments, the amount is from about 10 mg/kg to about 50 mg/kg. In some embodiments, the amount is from about 0.2 mg/kg to about 75 mg/kg. In some embodiments, the amount is from about 0.2 mg/kg to about 50 mg/kg. In some embodiments, the amount is from about 0.2 mg/kg to about 25 mg/kg. In some embodiments, the amount is from about 0.2 mg/kg to about 10 mg/kg. In some embodiments, the amount is from about 0.2 mg/kg to about 5 mg/kg. In some embodiments, the amount is from about 1 mg/kg to about 40 mg/kg. In some embodiments, the amount is from about 1 mg/kg to about 30 mg/kg. In some embodiments, the amount is from about 1 mg/kg to about 20 mg/kg. In some embodiments, the amount is from about 1 mg/kg to about 10 mg/kg. In some embodiments, the amount is from about 10 mg/kg to about 40 mg/kg. In some embodiments, the amount is from about 10 mg/kg to about 30 mg/kg. In some embodiments, the amount is from about 10 mg/kg to about 20 mg/kg. In any of the above methods or treatment protocols or regimens, the compound may be administered to the subject in an amount that is effective to displace the agent from the cancerous tissue without substantially displacing the agent from non-cancerous tissue.

In any of the above methods or treatment protocols or regimens or kits, and unless otherwise specified, the waiting period may be greater than or equal to 1 hour, greater than or equal to 2 hours, greater than or equal to 4 hours, greater than or equal to 6 hours, greater than or equal to 8 hours, greater than or equal to 10 hours, greater than or equal to 12 hours, greater than or equal to 14 hours, greater than or equal to 16 hours, greater than or equal to 18 hours, greater than or equal to 20 hours, greater than or equal to 22 hours, or greater than or equal to 24 hours. In some embodiments, the waiting period is from about 1 hour to about 60 hours. In some embodiments, the waiting period is from about 5 hours to about 36 hours. In some embodiments, the waiting period is about 24 hours. In some embodiments, the waiting period is about 48 hours.

In any of the above methods or treatment protocols or regimens or kits, and unless otherwise specified, the agent is capable of displacing the compound from non-cancerous tissue, while having a lesser effect of displacing the compound from the cancerous tissue. In some embodiments, the agent does not include a radionuclide. In some embodiments, the agent is a compound of the same structure as the compound without the radionuclide. In other words, the agent may be cold version of the compound. As used herein, a cold version of the compound is the compound without a radionuclide. Where the compound includes a metal chelation moiety, the cold version may be the free ligand, unchelated to a metal, or it may be chelated to a non-radioactive metal. Where the compound includes a radioactive non-metal, i.e., iodine, the cold version may be a non-radioactive iodine, or it may have a different group than iodine. In some embodiments, the recognition moiety of the agent includes a phosphinyl moiety.

The agent may be a more polar compound than the compound having the radionuclide.

In some embodiments, the agent has a recognition moiety for prostate specific membrane antigen. In some embodiments, the agent includes a Glu-Urea-based PSMA ligand.

In some embodiments, the agent may be a cold MIP-1555, MIP-1072, MIP-1095, MIP-1558, or MIP-1404, or the agent may include, but is not limited to, 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid;

2-[[cyclohexylhydroxyphosphinyl]methyl]pentanedioic acid; 2-[[phenylhydroxyphosphinyl]methyl]pentanedioic acid; 2-[[(phenylmethyl)hydroxyphosphinyl]methyl]pentanedioic acid; 2-[[((2-phenylethyl)methyl)hydroxyphosphinyl]methyl]pentanedioic acid; 2-[[((3-phenylpropyl)methyl)hydroxyphosphinyl]methyl]pentanedioic acid; 2-[[((3-phenylbutyl)methyl)hydroxyphosphinyl]methyl] pentanedioic acid; 2-[[((2-phenylbutyl)methyl)hydroxyphosphinyl]methyl]pentanedioic acid; 2-[[(4-phenylbutyl)hydroxyphosphinyl]methyl]pentanedioic acid; 2-[[(aminomethyl)hydroxyphosphinyl]methyl]pentanedioic acid; 7-(L-2-amino-2-carboxyethylthio)-2-(2,2-dimethylcyclopropanecarboxamide)-2-heptenoic acid; 2-(phosphonomethyl)pentanedioic acid; N-[methylhydroxyphosphinyl]glutamic acid; N-[ethylhydroxyphosphinyl]glutamic acid; N-[propylhydroxyphosphinyl]glutamic acid; N-[butylhydroxyphosphinyl]glutamic acid; N-[phenylhydroxyphosphinyl]glutamic acid; N-[(phenylmethyl)hydroxyphosphinyl] glutamic acid; N-[((2-phenylethyl)methyl)hydroxyphosphinyl]glutamic acid; N-methyl-N-[phenylhydroxyphosphinyl]glutamic acid; 2-(3-mercaptopropyl)pentanedioic acid (2-MPPA), a pharmaceutically acceptable salt thereof; or a mixture of any two or more thereof. In some embodiments, the agent includes 2-(phosphonomethyl)pentanedioic acid. In some embodiments, the agent includes cold MIP-1555, cold MIP-1519, cold MIP-1545, cold MIP-1427, cold MIP-1428, cold MIP-1379, cold MIP-1072, cold MIP-1095, cold MIP-1558, cold MIP-1405, or cold MIP-1404.

The agent may be administered to the subject in an amount that is effective to displace the compound from the non-cancerous tissue without substantially displacing the compound from cancerous tissue. The amount of the agent administered will depend upon the particular compound and radionuclide that are administered, and the type of agent that is administered. For example, but not by way of limitation, the amount of agent administered may be from about 0.2 mg/kg to about 100 mg/kg. In some embodiments the agent is administered from about 1 mg/kg to about 50 mg/kg. In yet other embodiments, the agent is administered to the subject from about 10 mg/kg to about 50 mg/kg. In some embodiments, the agent is administered to the subject from about 0.2 mg/kg to about 75 mg/kg. In some embodiments, the agent is administered to the subject from about 0.2 mg/kg to about 50 mg/kg. In some embodiments, the agent is administered to the subject from about 0.2 mg/kg to about 25 mg/kg. In some embodiments, the agent is administered to the subject from about 0.2 mg/kg to about 10 mg/kg. In some embodiments, the agent is administered to the subject from about 0.2 mg/kg to about 5 mg/kg. In some embodiments, the agent is administered to the subject from about 1 mg/kg to about 40 mg/kg. In some embodiments, the agent is administered to the subject from about 1 mg/kg to about 30 mg/kg. In some embodiments, the agent is administered to the subject from about 1 mg/kg to about 20 mg/kg. In some embodiments, the agent is administered to the subject from about 1 mg/kg to about 10 mg/kg. In some embodiments, the agent is administered to the subject from about 10 mg/kg to about 40 mg/kg. In some embodiments, the agent is administered to the subject from about 10 mg/kg to about 30 mg/kg. In some embodiments, the agent is administered to the subject from about 10 mg/kg to about 20 mg/kg.

The present invention, thus generally described, will be understood more readily by reference to the following examples, which are provided by way of illustration and are not intended to be limiting of the present invention.

EXAMPLES

Material and Methods. All animal studies were approved by the Institutional Animal Care and Use Committee in accordance with the guidelines for Care and Use of Laboratory Animals.

With regard to Examples 1-3, mice were housed under standard conditions in approved facilities with 12 hour light/dark cycles and given food and water ad libitum. BALB/c nude mice were implanted with $5 \times 10^6$ LNCaP cells (BD Biosciences) suspended in Matrigel (BD Biosciences) behind the left shoulder. The mice were used for our study after 8-12 weeks, when the tumors reached approximately 1.5 cm in diameter.

MIP-1095, MIP-1404, and MIP-1558. The synthesis of MIP-1095 (S)-2-(3-((S)-1-carboxy-5-(3-(4-iodophenyl)ureido)pentyl)ureido)pentanedioic acid, the radiolabeling precursor trimethyltin-MIP-1095 and the subsequent radiolabeling with a variety of iodine isotopes was described previously.[6,8] An illustrative structural representation of MIP-1095 is shown below as the $^{123}$I compound; however, as eluded to previously, other iodine isotopes such as $^{124}$I, $^{125}$I, and $^{123}$I may be used.

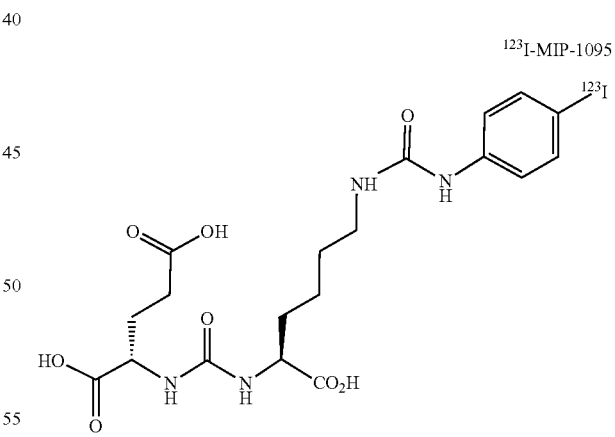

MIP-1404 and MIP-1558 were provided from Molecular Insight Pharmaceuticals (Tarrytown, N.Y., USA) and labeled with either $^{99m}$Tc (ELUMATIC III generator, IBA, Belgium) or $^{68}$Ga (Ga-Generator, iThemba LABS, Somerset West, South Africa). The synthesis of MIP-1404 has already been described previously.[9] The structure of MIP-1404 is illustrated below as a metal complexed "M" compound. The synthesis of MIP-1558 has already been previously described in WO 2014/110372. The structure of MIP-1558 is illustrated below as a metal complexed "M" compound.

MIP-1404

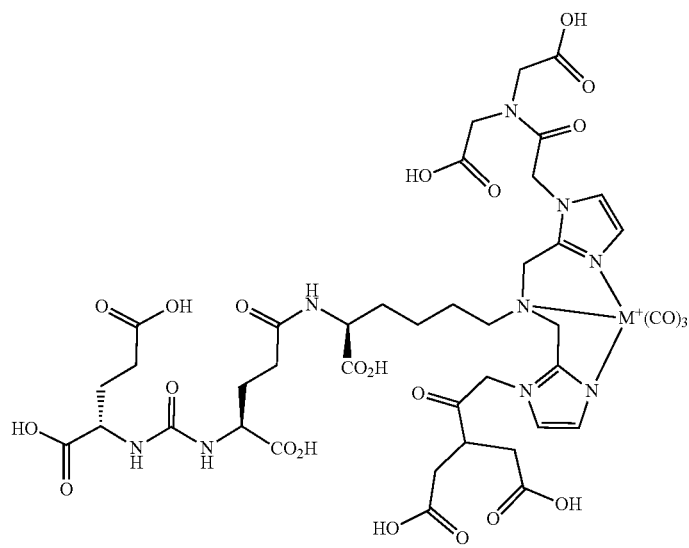

MIP-1558

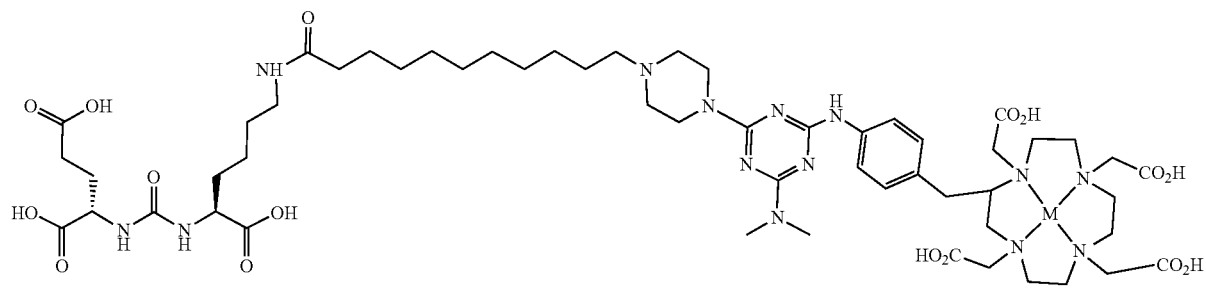

Example 1. Mice bearing LNCaP tumors of 1.5 cm diameter were injected via the tail vein with 37 MBq of $^{125}$I-MIP-1095 in 100 μl at a specific activity of >1,000 mCi/Amol. Mice were imaged at a baseline time of 16 hours post injection giving enough time for tracer clearance from the blood stream and kidney calices. Immediately after the baseline scan, PMPA in 100 μl physiological saline solution was injected via the tail vein in doses of 50 mg/kg, 10 mg/kg, 1 mg/kg, and 0.2 mg/kg (n=3, respectively), or the animals served as controls (n=5). Planar scans were obtained at 2 hours, 4 hours, 6 hours, and 24 hours (1 day) post PMPA injection. See FIG. 1A.

Example 2. MIP-1404 was evaluated after labeling with $^{99m}$Tc in LNCaP bearing BALB/c nude mice. The baseline scan was done 1 hour after injection of 9.3 to 11 MBq $^{99m}$Tc-MIP-1404 in 100 μl directly followed with the injection of 50 mg/kg PMPA in 50 μl or 50 μl saline (n=3, respectively). Planar scans were obtained 1 hour and 3 hours after the subsequent PMPA/saline injection. The flow chart of the experiment is presented in FIG. 3A. Quantification was done with kidney regions of interest (ROI) arising counts per minute (cpm) which were then converted to percentage-of-baseline values. The same protocol was used to evaluate kidney uptake of 10.3 to 11.6 MBq $^{99m}$Tc-MIP-1404 in 100 μl directly followed with the injection of 50 mg/kg, 10 mg/kg, and 1 mg/kg PMPA in 50 μl or saline as controls (n=4, respectively) in non-tumor bearing NMRI mice. In a pilot experiment planar scans after injection of the salivary gland tracer $^{99m}$Tc pertechnetate were acquired and the diagnostic value of the images was judged visually.

Example 3. MIP-1558 was evaluated after labeling with $^{68}$Ga and imaging in an animal PET. Due to the short half-life of $^{68}$Ga (68 min) the baseline scan was done 1 hour after injection of 9 to 28 MBq $^{68}$Ga-MIP-1558 in 100 μl into LNCaP tumor bearing BALB/c nude mice directly followed with the injection of 50 mg/kg PMPA (n=3) in 50 μl or an equivocal volume of saline as controls (n=3). Post-PMPA scans were acquired 1 hour and 2 hours after administration of PMPA. Both tumor and kidney uptake was determined in a volume of interest (VOI). Serial $^{68}$Ga-MIP-1558 PET scans were also done with three rats, once with saline and a few days later with serial co-injection of PMPA (10 mg/kg), for delineation of the salivary glands in larger animals.

Imaging. During imaging, mice were anesthetized using 1% isofluorane gas in oxygen flowing at 0.6 L/min. Serial planar scans were done with a Gamma Imager-sct (biospace labs, Paris, France). Quantification of tumor and kidney uptake was done by determining the counts per minute (cpm) in the target region by ROI-techniques. The baseline scan before administration of PMPA served as reference, the succeeding images are reported in percentage of the baseline value. PET scans were done with a dedicated small animal PET scanner (Siemens, Iveon) and quantification was done by VOI-techniques and reported as standardized uptake values (SUV).

Figure 1B:
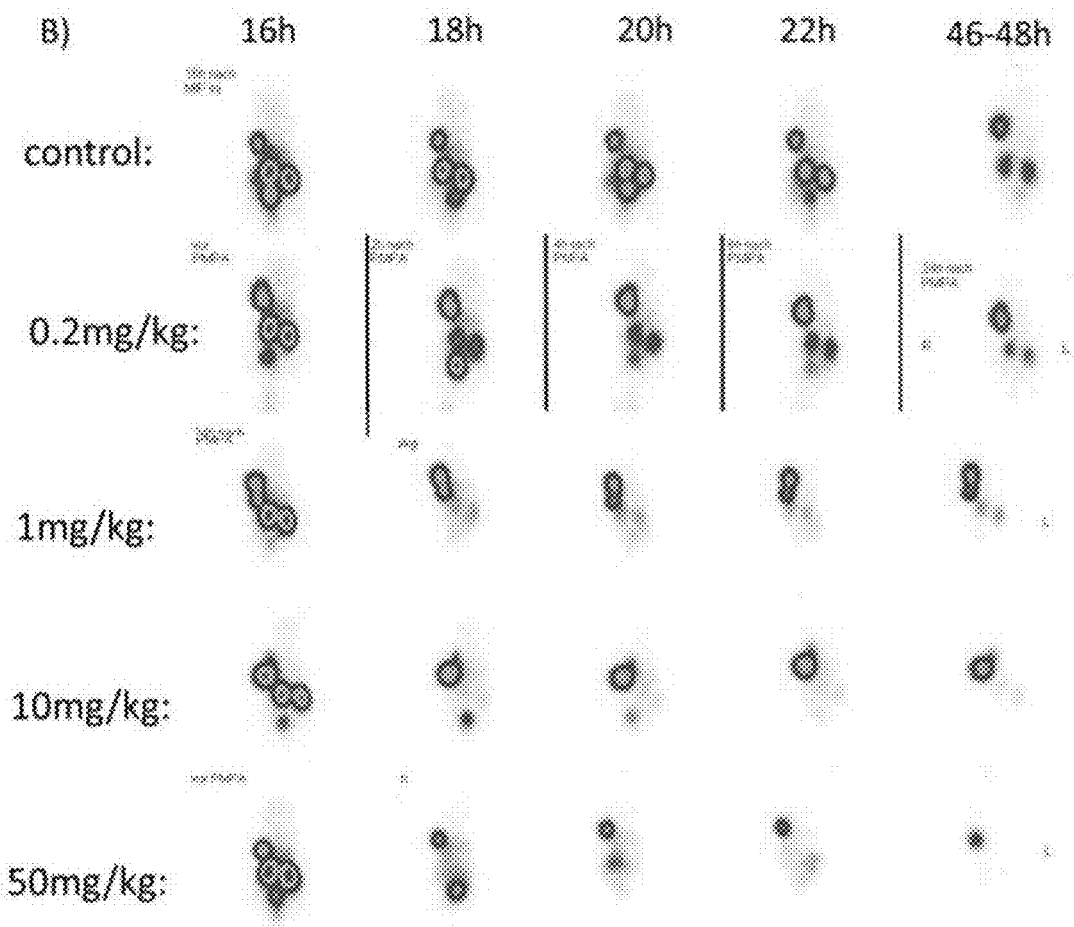
FIG. 1B shows scintigraphic images of controls and PMPA treated animals, according to the examples.
Figure 2A:
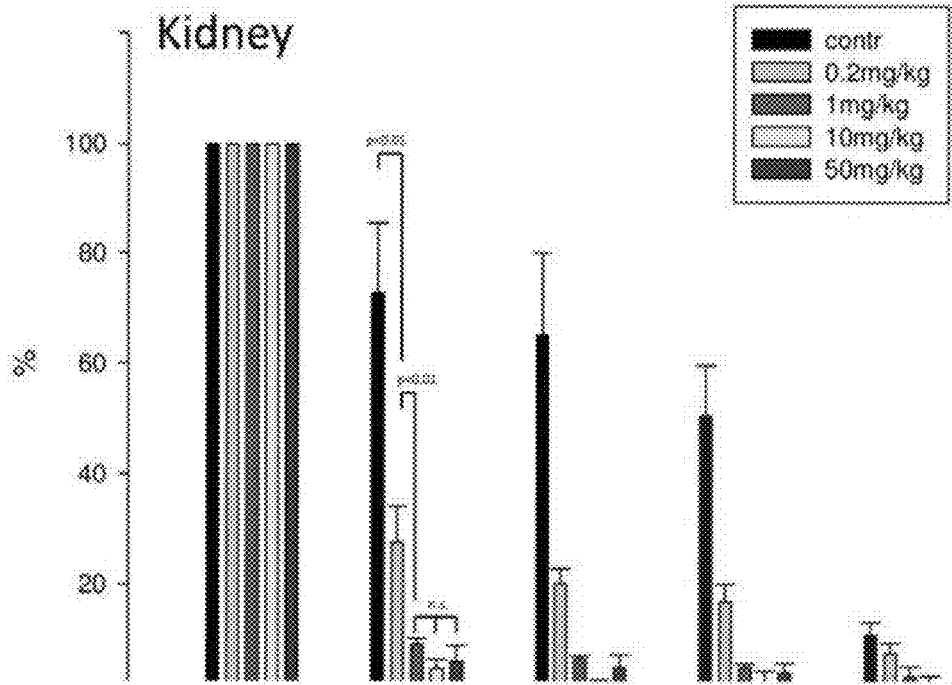
FIG. 2A is a time course of residual radioactivity in the kidney.
Figure 2B:
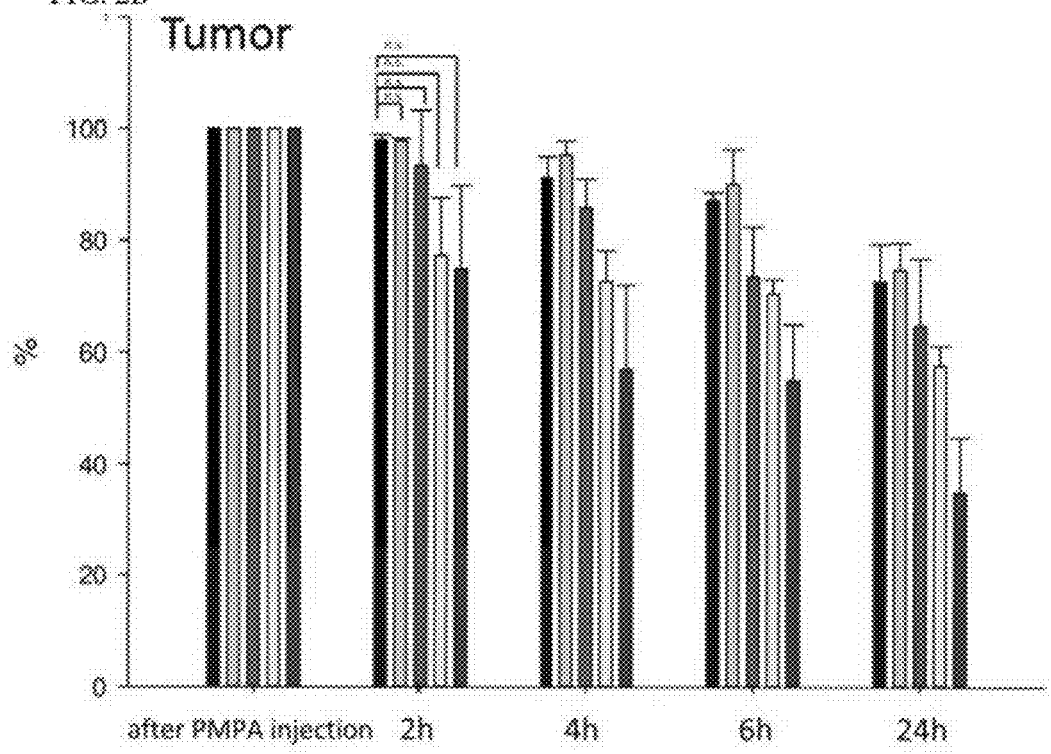
FIG. 2B is a time course of residual radioactivity in the tumor expressed in % of the value at 16 hours post injection of [$^{125}$I] MIP-1095 using different doses of PMPA, according to the examples.

Results. MIP1095: Subsequent injection of PMPA 16 hours after MIP-1095 translated into a rapid and quantitative relevant displacement of renal activity with all PMPA doses. Scintigraphy scans from one example out of each group are presented in FIG. 1B. The course of residual activity of $^{125}$I-MIP-1095 measured at the particular time points after subsequent administration of 0.2 mg/kg, 1 mg/kg, 10 mg/kg, and 50 mg/kg PMPA, or controls, are presented in FIG. 2A for kidney and FIG. 2B for tumor ROIs. Even at a very low dose of 0.2 mg/kg, there is a high significant (p<0.01) displacement from the kidneys. The effect was more pronounced at higher doses and showed a dose dependency with 1 mg/kg, thus revealing an even higher kidney washout than the 0.2 mg/kg dose (p<0.01). However, doses greater than 1 mg/kg did not improve the kidney-protective effect (i.e., the differences between 1 mg/kg, 10 mg/kg, and 50 mg/kg PMPA groups were not significant). In tumor tissue, the uptake of $^{125}$I-MIP-1095 was displaced by subsequent injection of PMPA. By visual observation, the effect appears to be dose dependent: residual uptake 2 hours after PMPA was 98% with 0.2 mg/kg, 93% with 1 mg/kg, 77% with 10 mg/kg, and 75% with 50 mg/kg. However, due to the small size of the group (n=3) none of the differences was statistically significant.

Figure 4A:
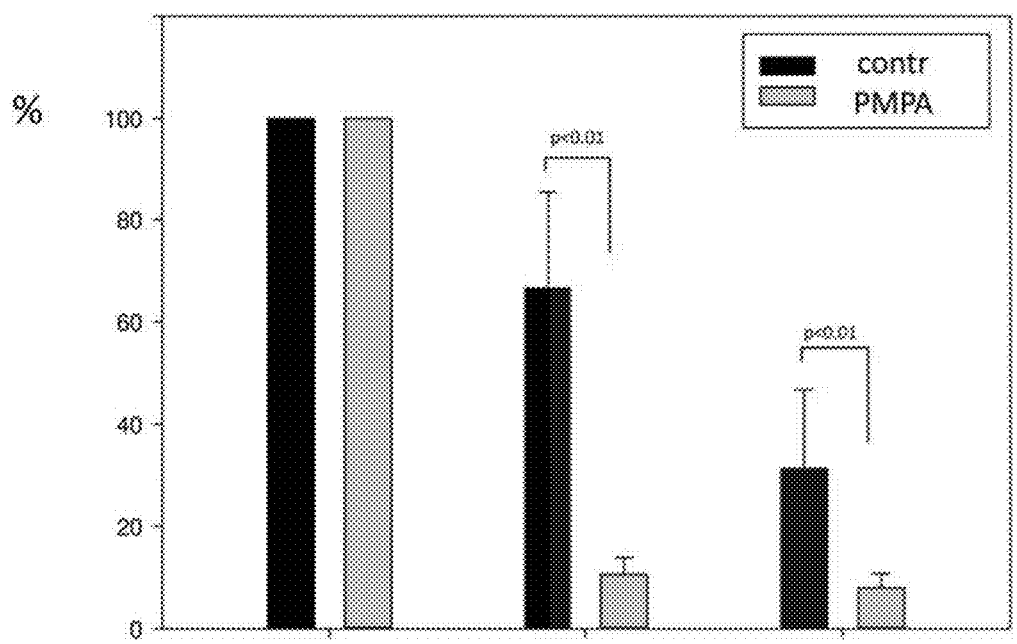
FIG. 4A is a time course of residual radioactivity in the kidney.
Figure 4B:
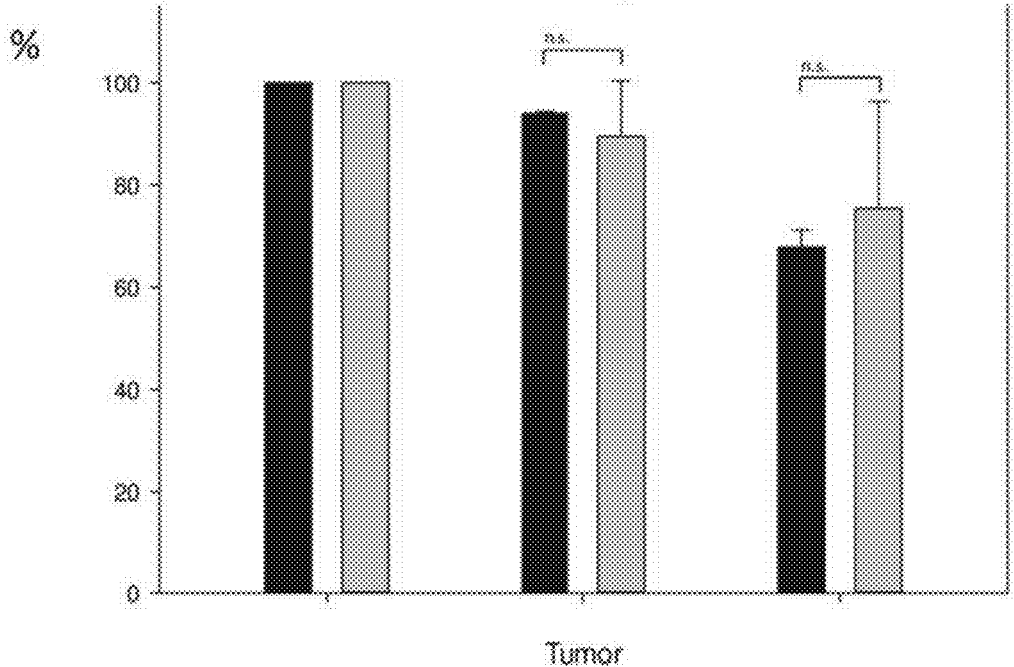
FIG. 4B is a time course of residual radioactivity in the tumor expressed in % of the value at 1 hour post-injection $^{99m}$Tc MIP-1404, according to the examples.

MIP-1404. Normalized to the 1 hour post injection tumor uptake there is a fast wash-out of MIP-1404 from the kidneys even without intervention. When 50 mg/kg PMPA was administered directly following the baseline scan, the washout from kidney was significantly (p<0.01) enhanced at 2 and 4 hours (FIG. 3B and FIG. 4A). In comparison to the controls, the difference in tumor uptake measured in the PMPA group was not significant, with the 50 mg/kg PMPA dose (FIG. 4B). As MIP-1404 seemed rather robust against tumor displacement even after high dose PMPA the dilution series with 10 mg/kg and 1 mg/kg were done in non-tumor bearing NMRI mice. Residual kidney uptake at 2 and 4 hours were 36% and 15%, respectively, in controls, 13% and 9%, respectively, after 1 mg/kg PMPA, 15 and 10%, respectively, after 10 mg/kg PMPA, and 11% and 7%, respectively, after 50 mg/kg PMPA. This pattern is in concert with the larger MIP-1095 series, with optimal kidney displacement even at 1 mg/kg and no benefit of higher PMPA doses. In a pilot study, planar scans of the mice were acquired after injection of $^{99m}$Tc pertechnetate which is known to accumulate in the salivary glands but due to the limited spatial resolution of the camera these small structures were not able to be sufficiently delineated in the mice.

MIP-1558: In controls, the mean tumor uptake of $^{68}$Ga-MIP1558 was 1 hour post injection SUVmax 0.95, 2 hours post injection SUVmax 1.25, and 3 hours post injection SUVmax 1.24. The 1 hour post injection baseline scan of the PMPA group was quite similar with a mean tumor uptake with an SUVmax of 0.94. Following administration of 50 mg/kg PMPA, the 2 hours post injection SUVmax decreased to a mean of 0.40, and the 3 hours post injection SUVmax decreased to 0.39. The corresponding kidney uptake in controls vs. PMPA at 1 hour, 2 hours, and 3 hours post injection were SUVmax values of 5.83 vs 7.13, 3.13 vs 1.87, and 2.60 vs 1.77, respectively. When examining the salivary region in the rats, a spontaneous SUVmax of mean 0.95 at 1 hour post injection, and 0.24 at 3 hours post injection was observed, thus, the perfusion dependency seems large in comparison to the specific long term binding. In the PMPA experiment an SUVmax of mean 0.82 at 1 hour post injection and 0.23 at 3 hours post injection were observed, thus, there does not appear to be a measurable change due to the PMPA intervention. However, on the later time points the salivary glands were hardly delineable compared to the background noise. It is believed that in larger animals and humans, that salivary gland, lacrimal gland, and parotid gland differentiation will be observable.

Discussion. The data demonstrate that injection of PMPA following an induction period after radionuclide therapy administration, provides for radiation dose limiting kidney uptake, and, possibly radiation dose limiting uptake by the salivary, lacrimal, and parotid glands. A relevant kidney displacement was observed independent of whether the evaluated tracer included a chelate (MIP-1404, MIP-1558) or not (MIP-1095). In addition to some nonspecific kidney uptake due to tubular reabsorption which might be further improved by modifications affecting the chelate or linker of the tracer molecule, a relevant part of kidney uptake seems to be related to specific PSMA binding.

PSMA is an emerging target for imaging and radionuclide therapy of metastasized PCa. Radionuclide therapy compounds such as, but not limited to, MIP-1095, MIP-1404 and MIP-1558, are currently among the most promising PSMA-ligands. The promise is attributed to: (a) fast tumor targeting, (b) fast clearance from untargeted organs, and (c) sufficient residency times in tumor tissue due to ligand-induced cellular internalization. MIP-1404 is of particular interest because it is a single amino acid chelator (SAAC) that can be either labeled with diagnostic $^{99m}$Tc or in therapeutic intention with $^{186}$Re or $^{188}$Re. Technetium and rhenium are chemically related and share structural as well as reactive similarities. $^{99m}$Tc is available from approved generator systems and can be imaged with the numerous already installed Anger cameras (i.e., gamma camera or scintillation camera). $^{186}$Re (half-life 3.7 days, max. energy of beta-emission 1.07 MeV, 11% co-emission of 137 keV gammas for imaging) presents an attractive "matched pair" for therapy. $^{188}$Re (half-life 17 h, max. energy of beta-emission 2.12 MeV, 15% co-emission of 155 keV gammas for imaging) can be obtained from a $^{188}$W/$^{188}$Re generator system (Oak Ridge National Laboratory) which was FDA approved and would be suitable for clinical application. MIP-1558 is clinically interesting because its DOTA (1,4,7,10-tetraaza-cyclododecane-1,4,7,10-tetraacetic acid) chelate can be labeled with the generator product $^{68}$Ga for PET-imaging or $^{111}$In for pre-therapeutic dosimetry studies. Numerous beta and alpha particle emitters—e.g. $^{90}$Y, $^{177}$Lu, $_{213}$Bi, $^{225}$Ac—are promising "matched pairs" for therapy [KRAC CCR2011, EJNM2014]. MIP-1095 can be tagged with different isotopes of iodine. Labeled with $^{125}$I (half-life 60 days, gamma emission 27-35 keV), MIP-1095 presents the best characteristics for small animal imaging, and, therefore, it was chosen for the main experiment.

It is common practice to show specific binding of PSMA ligands by simultaneous coinjection of 50 mg/kg PMPA which results in a complete blocking of MIP-1095 binding sites in tumor and kidneys.[3,11] Our findings now implicate, that a subsequent injection of the competitor, or blocking agent, does not significantly displace the endosome-fixed ligand from tumor, while displacing the non-internalized ligands from the kidneys and the salivary, lacrimal, and parotid glands.

The salivary glands present another organ with a high uptake of diagnostic PSMA-tracers and also to $^{131}$I-MIP-1095. In the present small animal imaging experiments, sufficient delineation of the salivary glands was not possible by scintigraphy or even dedicated small animal PET of rats. Therefore, the situation in salivary glands is rather unclear. However, if PSMA expression is responsible for tracer accumulation in the salivary glands, PMPA, or other agents/blockers may also be suitable to displace radioactive PSMA ligands from these organs and, as such, treat xerostomia side effects of PSMA targeted radionuclide therapy.

With regard to kidneys, a dose of PMPA in the range of 0.2 to 1.0 mg/kg was used. A dose of 1.0 mg/kg translates into near total renal displacement with only minimal (<10%) effect on tumor uptake. With 0.2 mg/kg the decrease in tumor uptake was <5%, but still a relevant improvement of kidney uptake could be observed. Nevertheless, renal activity was only sub-totally displaced with the lower dose. Doing a conservative, body surface based, extrapolation from the 0.2 mg/kg mouse dose to men, an 80 kg patient should receive about 60 mg of PMPA.

The orally bioavailable PSMA-inhibitor 2-(3-mercaptopropyl)pentanedioic acid (2-MPPA) which is nearly as potent as 2-(phosphonomethyl)pentanedioic acid (2-PMPA)—$IC_{50}$ 85 nM vs. 30 nM[12]—was already evaluated in 25 healthy subjects with a mean body weight of 71 kg. Doses of up to 750 mg (i.e., ~10 mg/kg) were found safe and generally well tolerated.

Example 4. The effect of cold MIP-1095 on the distribution of $^{125}$I-MIP-1095 in subcutaneously-implanted LNCaP xenografts in male Taconic Nude mice (CrTac:NCr-Foxn1$^{nu}$) using an automated gamma-counter was evaluated. Blood and tissues were collected 18 hours after intravenous injection of $^{125}$I-MIP-1095 (2 hours after displacing agent injections). Gamma-counter readouts were obtained for each sample and expressed as percent injected dose per gram of tissue using gamma-counter readout of the dosing solution as a reference.

PMPA was formulated in a vehicle of sterile saline. For dosing of the 0.50 mg/kg group, the PMPA was placed into a sterile vial and the appropriate amount of saline was added and mixed well by vortexing to form a clear solution with a pH value of 3.56. The dosing solution was prepared fresh the day of administration.

Cold MIP-1095 was stored protected from light at −80° C. until use. The compound was formulated in a vehicle of sterile saline. For dosing of the 0.50 mg/kg group, the cold MIP-1095 was placed into a sterile vial and the appropriate amount of saline was added and mixed well by vortexing to form a clear solution with a pH value of 6.96. Dosing solutions for the 0.15 mg/kg and 0.05 mg/kg groups were prepared by direct (not serial) dilution of the dosing solution from the 0.5 mg/kg group with complete vehicle. The dosing solutions were prepared fresh the day of administration.

$^{125}$I-MIP-1095 was frozen on dry ice with an activity concentration of 0.2 mCi/ml, and stored at −80° C. until use. For dosing, the stock solution (colorless) was thawed in a 37° C. water bath and diluted 1:1 with sterile saline for a fixed 0.1 mCi/ml solution for dosing. Additionally, it was spiked with cold MIP-1095 to a final concentration 0.00125 mg/mL. This approximately corresponded to a chemical mass associated with the therapeutically-active dose of $^{131}$I-MIP-1095 (body surface area-corrected).

LNCaP (clone FGC) cells were obtained from ATCC. They were grown in RPMI 1640 medium which was modified with 1% 100 mM Na pyruvate, 1% 1M HEPES buffer, 2.5 g/L Glucose and supplemented with 10% non-heat-inactivated Fetal Bovine Serum (FBS) and 1% 100× Penicillin/Streptomycin/L-Glutamine (PSG). The growth environment was maintained in an incubator with a 5% $CO_2$ atmosphere at 37° C. When expansion was complete, the cells (passage 4) were trypsinized using 0.25% trypsin-EDTA solution. Following cell detachment, the trypsin was inactivated by dilution with complete growth medium and any clumps of cells were separated by pipetting. The cells were centrifuged at 200 rcf for 10 minutes at 4° C., the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna automated cell counter. The pre-implantation cell viability was 97%. The cell suspension was centrifuged at 200 rcf for 10 minutes at 4° C. The supernatant was aspirated and the cell pellet was re-suspended in cold 50% serum-free medium: 50% Matrigel® to generate a final concentration of 2.50E+07 trypan-excluding cells/ml. The cell suspension was maintained on wet ice during implantation. Following implantation, an aliquot of the remaining cells was diluted with a trypan blue solution and counted to determine the post-implantation cell viability (96%).

Test animals were implanted subcutaneously, high in the axilla (just under the fore limb) on Day 0 with 5.0E+06 cells in 0.2 ml of 50% serum-free medium: 50% Matrigel® using a 27-gauge needle and syringe.

All mice were sorted into study groups based on caliper measurement estimation of tumor burden. The mice were distributed to ensure that the mean tumor burden for all groups was within 10% of the overall mean tumor burden for the study population. Treatment began on Day 25. Mice were administered test agent via intravenous injections. The mice were administered a fixed volume injection of 100 μl (approximately 4 ml/kg) via the tail vein, using a 28-gauge needle and insulin syringe. A fresh needle and syringe was used for each mouse.

Group 1—$^{125}$I-MIP-1095+Saline, 0.4 mCi/kg (0.005 mg/kg)+100 μl fixed volume, IV+IV, "Control"; test article at 0 hours, saline 16 hours post test article.
Group 2—$^{125}$I-MIP-1095+PMPA, 0.4 mCi/kg (0.005 mg/kg)+0.5 mg/kg, IV+IV, "Positive control"; test article at 0 hours, PMPA 16 hours post test article.
Group 3—$^{125}$I-MIP-1095+Cold MIP-1095 (conc.1), 0.4 mCi/kg (0.005 mg/kg)+0.05 mg/kg, IV+IV, test article at 0 hours, cold MIP-1095 (conc. 1) 16 hours post test article.
Group 4—$^{125}$I-MIP-1095+Cold MIP-1095 (conc.2), 0.4 mCi/kg (0.005 mg/kg)+0.15 mg/kg, IV+IV, test article at 0 hours, cold MIP-1095 (conc. 2) 16 hours post test article.
Group 5—$^{125}$I-MIP-1095+Cold MIP-1095 (conc.3), 0.4 mCi/kg (0.005 mg/kg)+0.5 mg/kg, IV+IV, test article at 0 hours, cold MIP-1095 (conc. 3) 16 hours post test article.

At 18 hours after the $^{125}$I-MIP-1095 dose, 5 mice per group, in numerical order, were euthanized for blood and tissue collection. Dosing times were staggered to allow for sample collection. All mice were euthanized via over exposure to carbon dioxide. Whole blood was collected via cardiac puncture and placed to a cylindrical test tube for gamma counting. After whole blood collection, the following tissues were excised: heart, lungs, liver, spleen, salivary glands, kidneys, stomach (with contents), large intestine (with contents), small intestines (with contents), testes, quadriceps (from right hind limb), femur (from right hind limb), brain, trachea/thyroid, adipose, and tumor. Each tissue was placed into a tared, cylindrical test tube and tissue wet weights were recorded. All mice were necropsied as they exited the study.

Figure 5:
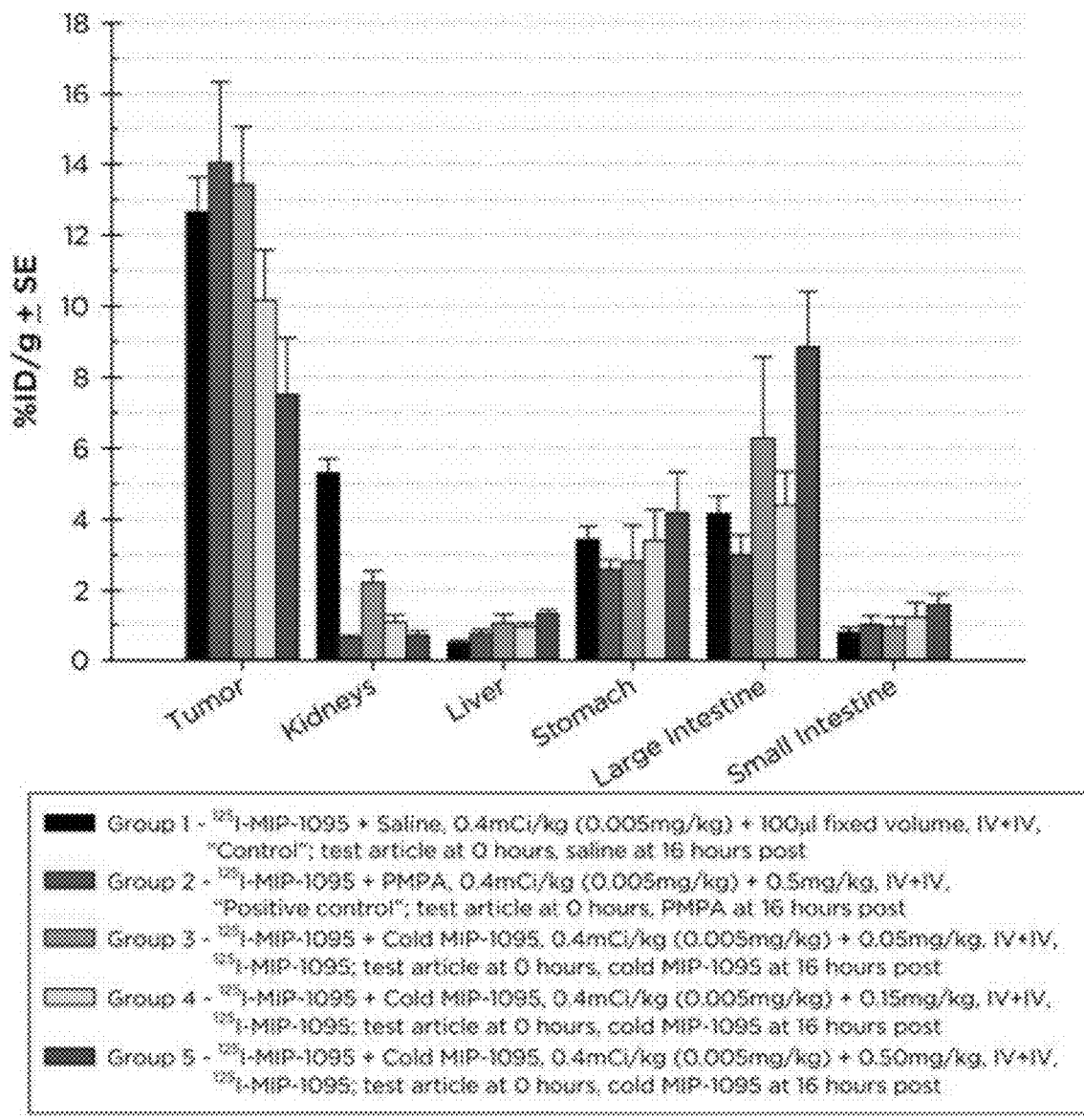
FIG. 5 is a chart showing ex vivo gamma counting values by tissue (% ID/g).
Figure 6:
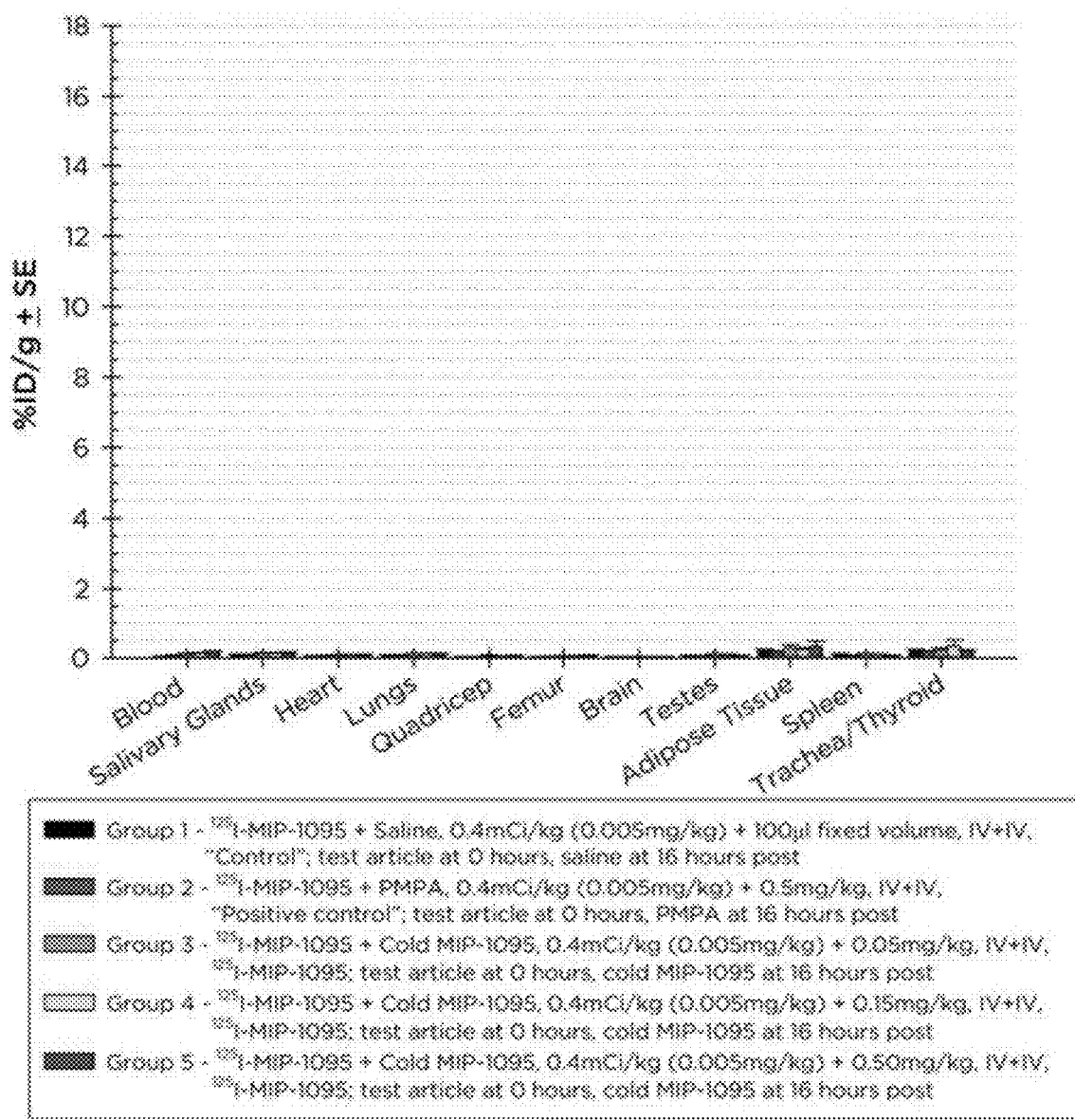
FIG. 6 is a chart showing ex vivo gamma counting values by tissue (% ID/g).

The samples were then transported to the gamma counter, where samples were counted for sixty seconds using a PerkinElmer WIZARD$^2$ gamma counting system. A 100 μl standard aliquot (1 dose) of the $^{125}$I-MIP-1095 dosing solution was also measured along with the tissues. This aliquot was intended to represent the total injected dose for mice to enable a simplified calculation of percent injected dose (% ID). The % ID was calculated as the ratio of the total individual tissue counts to the total counts acquired from the standard aliquot×100. % ID/g was calculated by dividing the % ID by the tissue wet weight in grams, as measured at the time of sampling. There was a time delay between sample collections and gamma counting, the measured activity values were corrected for decay as needed. See FIGS. 5 and 6.

Results/Discussion. In the negative control group (group 1; saline), LNCaP tumors showed the highest exposure of $^{125}$I-MIP-1095 followed by kidneys, stomach, small and large intestines, and liver. All other tissues and organs (including salivary glands) showed the exposure less than 1% of ID/g. It appears that mouse is a suitable model to evaluate the displacing effect in the kidneys but not a suitable model for salivary glands which is another potential organ for radiation toxicity associated with $^{131}$I-MIP-1095 therapy (see Eur. J. Nucl. Med. Mol. Imaging. 2014 July; 41(7): 1280-92).

In the positive control group (group 2; 0.5 mg/kg PMPA), the displacing agent greatly reduced exposure of $^{125}$I-MIP-1095 in the kidneys while the exposure in LNCaP tumors and all other organs and tissues was little changed. These results are in good correlation with the literature-reported data (see J. Nucl. Med. 2015 February; 56(2):293-8).

In the test article groups (groups 3, 4 and 5; cold MIP-1095 at 0.05, 0.15 and 0.5 mg/kg, respectively), the displacing agent dose-dependently reduced $^{125}$I-MIP-1095 kidney exposure. At the highest dose, the reduction in kidney exposure was equivalent to the one observed for positive control. The reduction in kidney exposure, however, was accompanied by a dose-dependent decrease in LNCaP tumors exposure and a dose-dependent increase in liver, stomach, large and small intestines exposure. The changes in tumor and normal organs exposure were not as pronounced as changes in kidney exposure. For example, in group 4, the kidney exposure was reduced 5-fold compared to negative control while LNCaP tumors exposure was reduced only 1.2-fold while exposure in other organs was little changed.

Overall, the study results indicated that with careful dose selection it is possible to meaningfully reduce kidney exposure by administering a cold MIP-1095 several hours post $^{125}$I-MIP-1095 dose while maintaining a reasonably high tumor exposure and keeping all other organs exposure relatively unchanged.

REFERENCES

1. Silver, D. A. et al. *Clin. Cancer Res.* 3(1):81-5 (1997).
2. Ross, J. S. et al. *Clin. Cancer Res.* 15; 9(17):6357-62 (2005).
3. Eder, M. et al. *Eur. J. Nucl. Med. Mol. Imaging* 40(6): 819-23 (2013).
4. Rosenthal, S. A. et al. *Tech. Urol.* 7(1):27-37 (2001).
5. Vallabhajosula, S. et al. *J. Nucl. Med.* 46:634-41 (2005).
6. Tagawa, S. T. et al. *Clin. Cancer Res.* 19(18):5182-91 (2013).
7. Barrett, J. A. et al. *J. Nucl. Med.* 54(3):380-7 (2013).
8. Afshar-Oromieh, A. et al. *Eur. J. Nucl. Med. Mol. Imaging* 40(4):486-95 (2013).
9. Afshar-Oromieh, A et al. *Eur. J. Nucl. Med. Mol. Imaging* 41(1):11-20 (2014).
10. Zechmann, C. M. et al. *Eur. J. Nucl. Med. Mol. Imaging* Feb. 28, 2014. E-published ahead of print.
11. Hillier, S. M. et al. *Cancer Res.* 69(17):6932-40 (2009).
12. Maresca, K. P. et al. *J. Med. Chem.* 52(2):347-57 (2009).
13. Hillier, S. M *J. Nucl. Med.* 54(8):1369-76 (2013).
14. Argyrou, M. et al. *Int. J. Mol. Imaging* 2013:290750 (2013).
15. Hlouchová, K. et al. *J. Neurochem.* 101(3):682-96 (2007).
16. Tsukamoto, T. et al. *J. Med. Chem.* 48(7):2319-24 (2005).
18. She, Y. et al. *J. Clin. Oncol.* 16S:8054 (2005).
19. Mhawech-Fauceglia, P. et al. *Histopathology* 50(4):472-83 (2007).
20. Wolf, P. et al. *Prostate* 70(5):562-9 (2010).
21. Anilkumar, G. et al. *Cancer Res.* 63:2645-48 (2003).
22. Pangalos, M. N. et al. *J. Biol. Chem.* 274:8470-8483 (1999).
23. Hlouchova, K. et al. *J. Neurochem.* 101:682-696 (2007.
24. Barinka, C. et al. *J. Neurochem.* 80:477-487 (2002).
25. Ghosh, A. et al. *Prostate* 57:140-151 (2003).
26. Rovenská, M. et al. *Prostate* 68(2):171-82 (2008).
27. Liu, H. et al. *Cancer Res.* 58:4055-4060 (1998).
28. Olson, W C. et al. *Front Biosci (Landmark Ed)* 19:12-23 (2014)
29. Israeli, R S, et al *Cancer Research* 54:1807-1811 (1994)
30 Troyer, J K et al Int. J. Cancer 62:552-558 (1995).

EQUIVALENTS

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A therapeutic radionuclide regimen for treating cancerous prostate tissue in a subject, the regimen comprising administering an agent to the subject and after allowing a waiting period of 1 hour to 60 hours to pass administering a compound comprising a recognition moiety for Prostate Specific Membrane Antigen ("PSMA") and a radionuclide to a subject harboring the cancerous prostate tissue; wherein:

the compound binds to both cancerous prostate tissue and non-cancerous tissue;
the compound is administered in an amount sufficient to cause a displacement of the agent in cancerous tissue;
the agent does not include a radionuclide;
the compound is a Glu-urea-based PSMA ligand; and
the agent comprises a Glu-urea-based PSMA ligand, a phosphinyl containing moiety, 7-(L-2-amino-2-carboxyethylthio)-2-(2,2-dimethylcyclopropanecarboxamide)-2-heptenoic acid, 2-(phosphonomethyl)pentanedioic acid, or 2-(3-mercaptopropyl)pentanedioic acid (2-MPPA).

2. The regimen of claim 1, wherein the non-cancerous tissue is kidney tissue, salivary gland tissue, lacrimal gland tissue, parotid gland tissue, or small intestine tissue.

3. The regimen of claim 1, wherein the radionuclide is a radioactive isotope of Ga, I, Y, Lu, Bi, Ac, Re, In, Th, or Tc.

4. The regimen of claim 1, wherein the compound is:

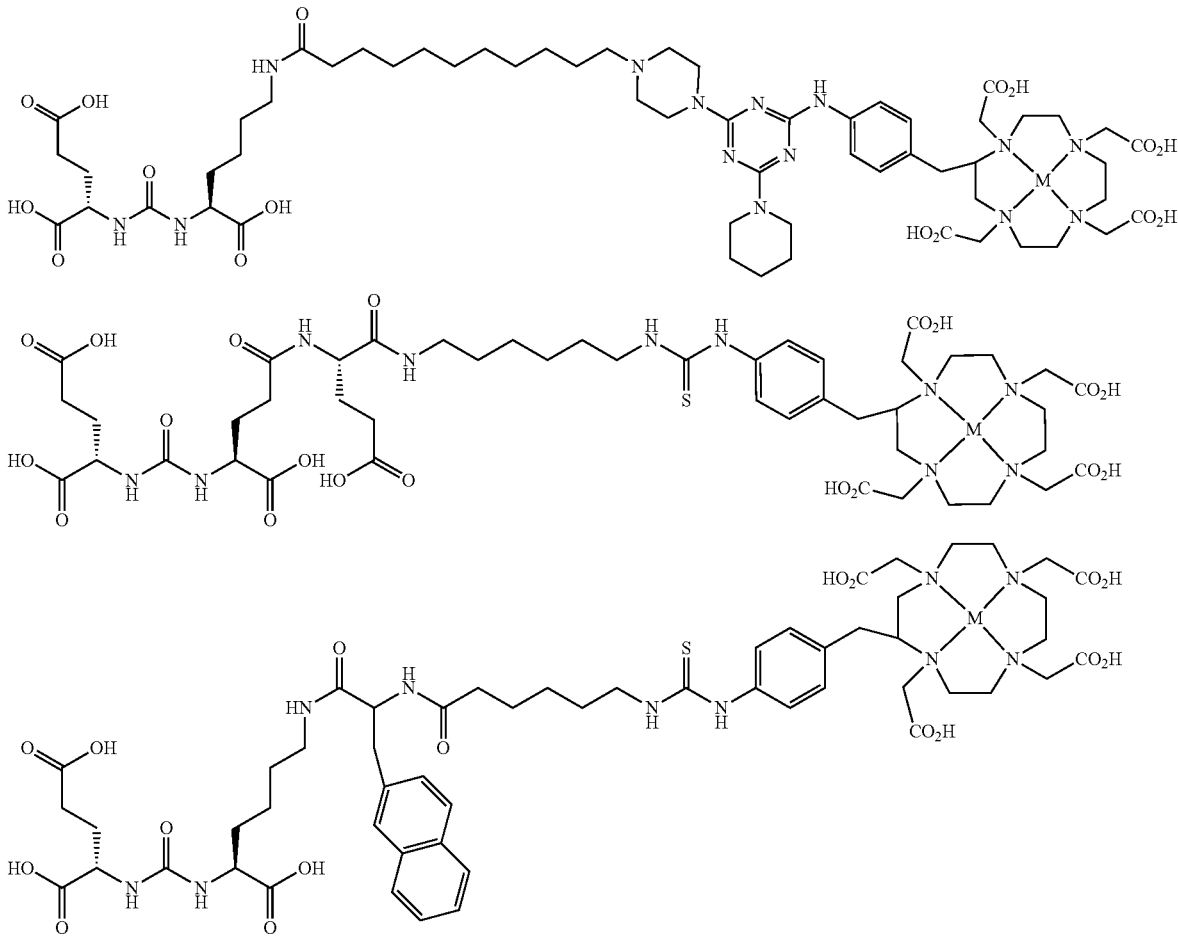

-continued
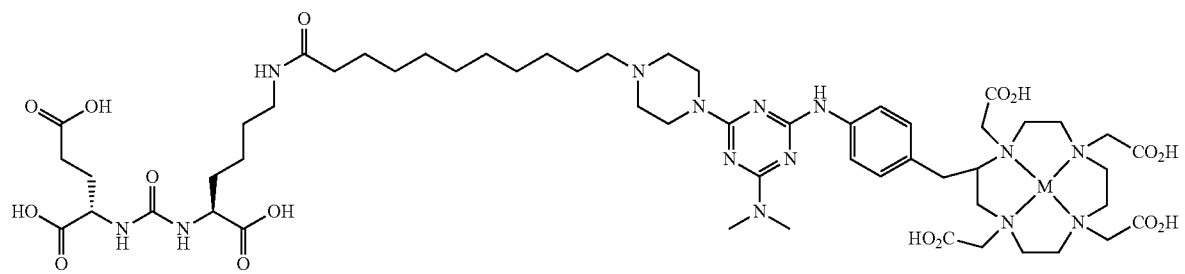
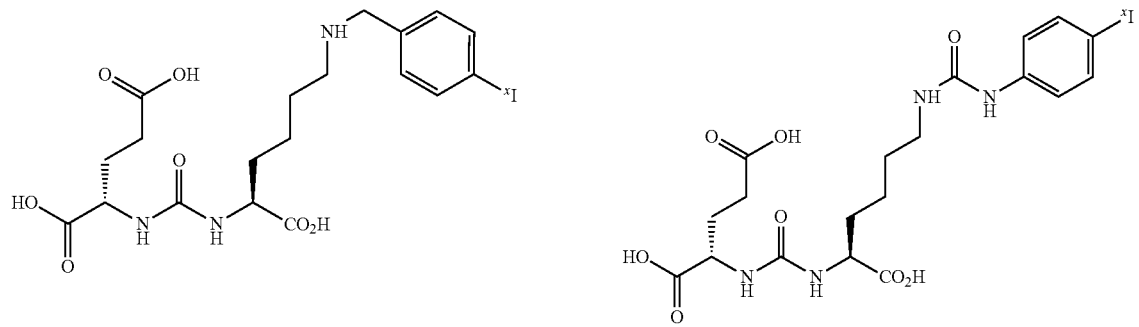
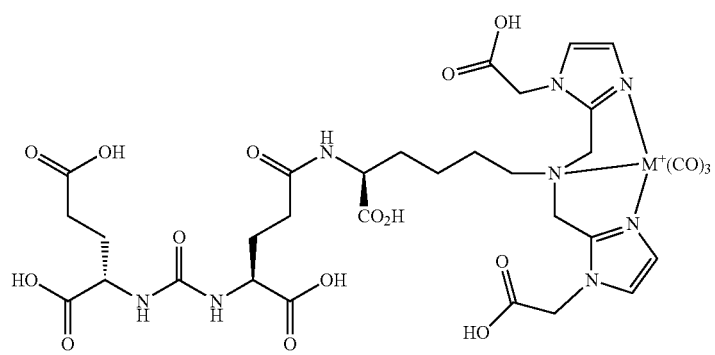
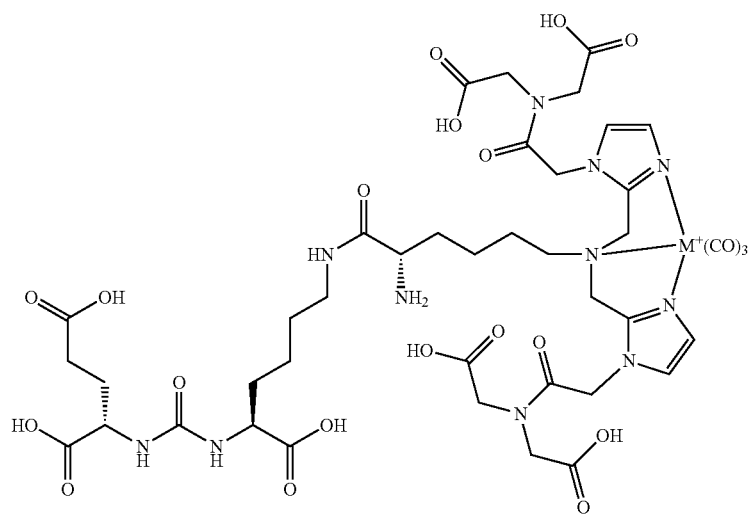

-continued

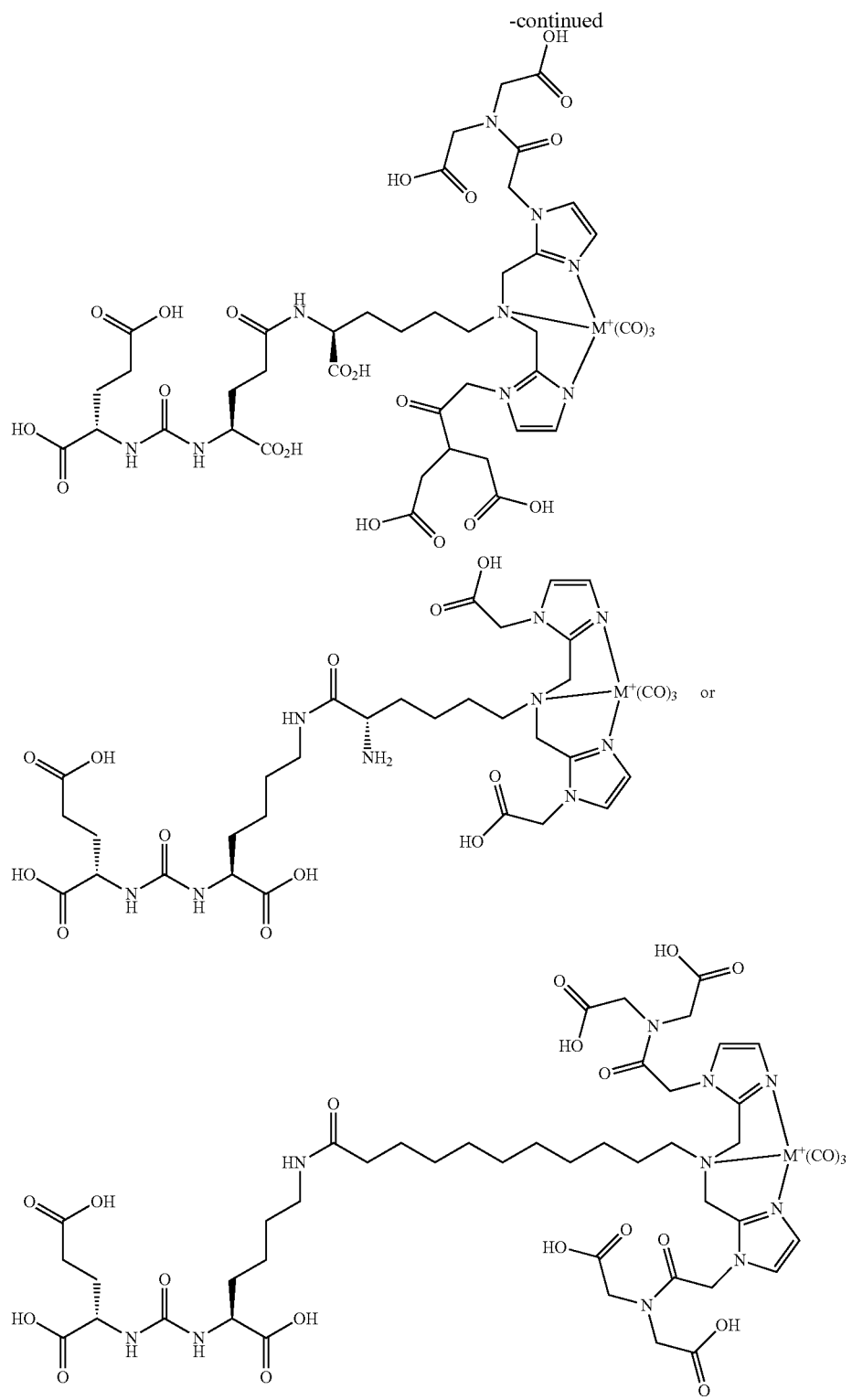

and wherein M is a radionuclide and $^xI$ is a radionuclide of iodine.

5. The regimen of claim 1, wherein the agent comprises: 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid; 2-[[cyclohexylhydroxyphosphinyl]methyl]pentanedioic acid; 2-[[phenylhydroxyphosphinyl]methyl]pentanedioic acid; 2-[[(phenylmethyl)hydroxyphosphinyl]methyl]pentanedioic acid; 2-[[((2-phenylethyl)methyl)hydroxyphosphinyl]methyl]pentanedioic acid; 2-[[((3-phenylpropyl)methyl)hydroxyphosphinyl]methyl]pentanedioic acid; 2-[[((3-phenylbutyl)methyl)hydroxyphosphinyl]methyl]

pentanedioic acid; 2-[[((2-phenylbutyl)methyl)hydroxyphosphinyl]methyl]pentanedioic acid; 2-[[(4-phenylbutyl)hydroxyphosphinyl]methyl]pentanedioic acid; 2-[[(aminomethyl)hydroxyphosphinyl]methyl]pentanedioic acid; 7-(L-2-amino-2-carboxyethylthio)-2-(2,2-dimethylcyclopropanecarboxamide)-2-heptenoic acid; 2-(phosphonomethyl)pentanedioic acid; N-[methylhydroxyphosphinyl]glutamic acid; N-[ethylhydroxyphosphinyl]glutamic acid; N-[propylhydroxyphosphinyl]glutamic acid; N-[butylhydroxyphosphinyl]glutamic acid; N-[phenylhydroxyphosphinyl]glutamic acid; N-[(phenylmethyl)hydroxyphosphinyl] glutamic acid; N-[((2-phenylethyl)methyl)hydroxyphosphinyl]glutamic acid; N-methyl-N-[phenylhydroxyphosphinyl]glutamic acid; 2-(3-mercaptopropyl)pentanedioic acid (2-MPPA), a pharmaceutically acceptable salt thereof; or a mixture of any two or more thereof.

6. The regimen of claim 1, wherein the agent is cold MIP-1555, cold MIP-1519, cold MIP-1545, cold MIP-1427, cold MIP-1428, cold MIP-1379, cold MIP-1072, cold MIP-1095, cold MIP-1558, cold MIP-1405, or cold MIP-1404; wherein:

MIP-1555

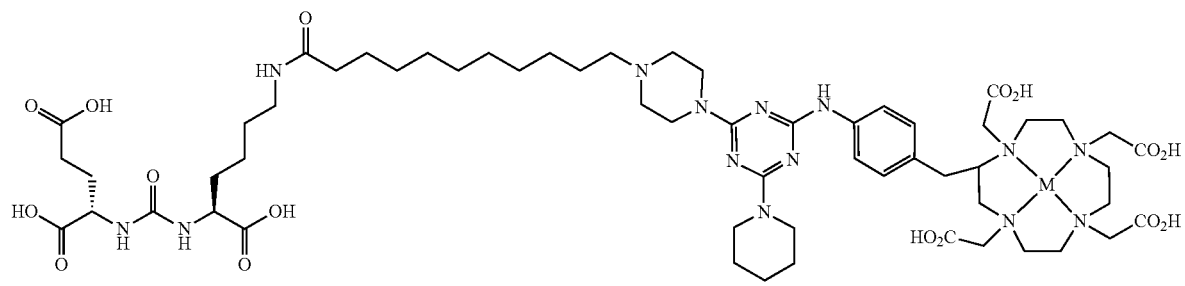

MIP-1519

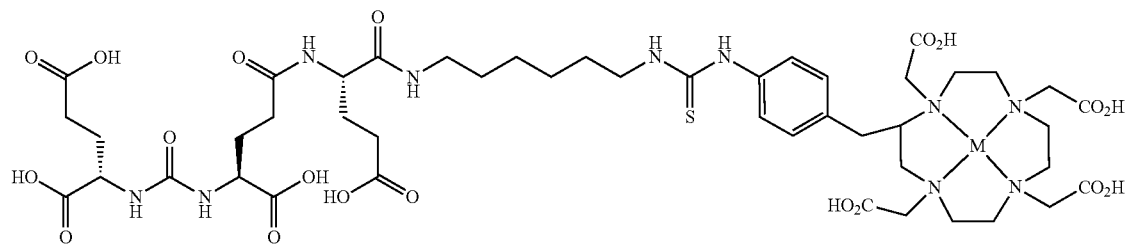

MIP-1545

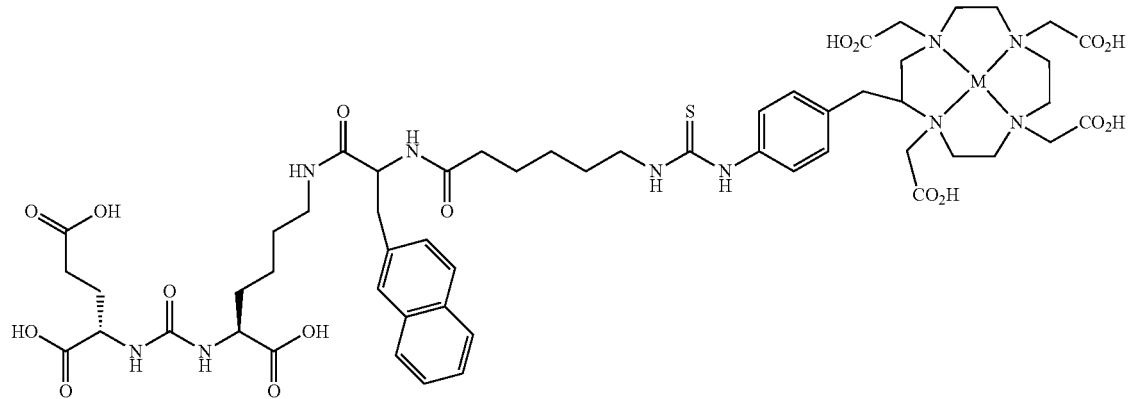

MIP-1558

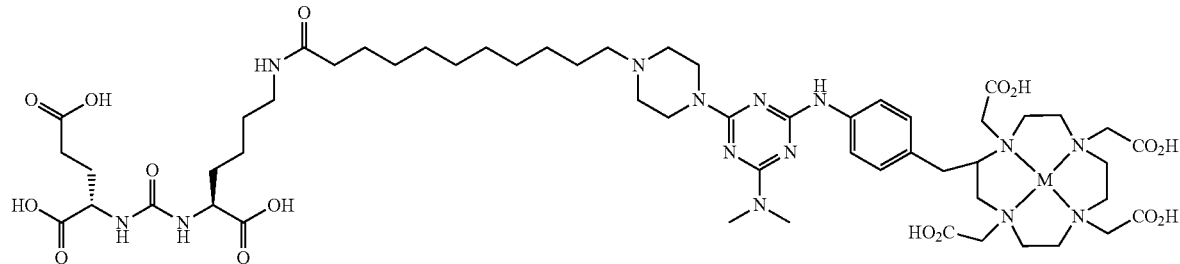

-continued
MIP-1072
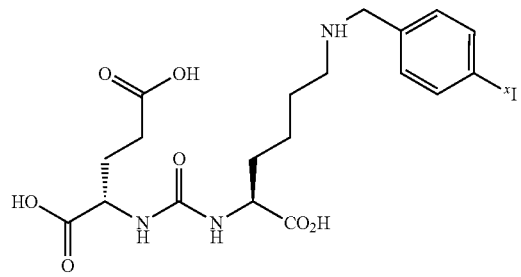
MIP-1095
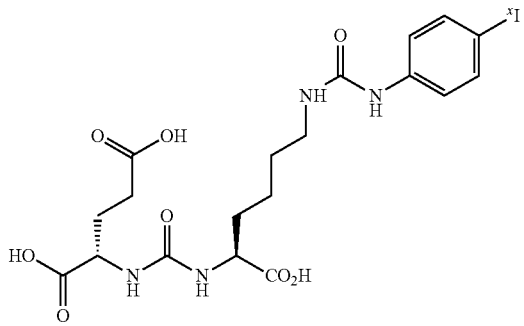
MIP-1427
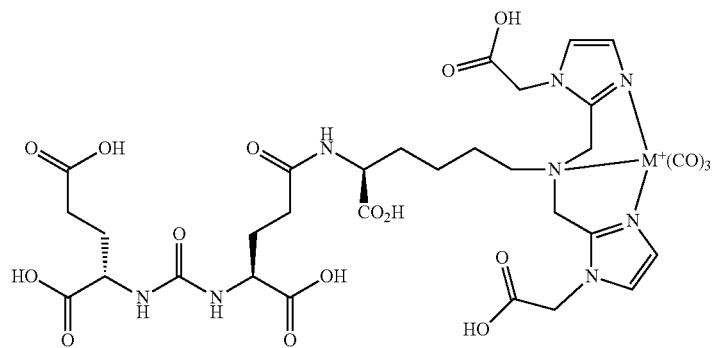
MIP-1428
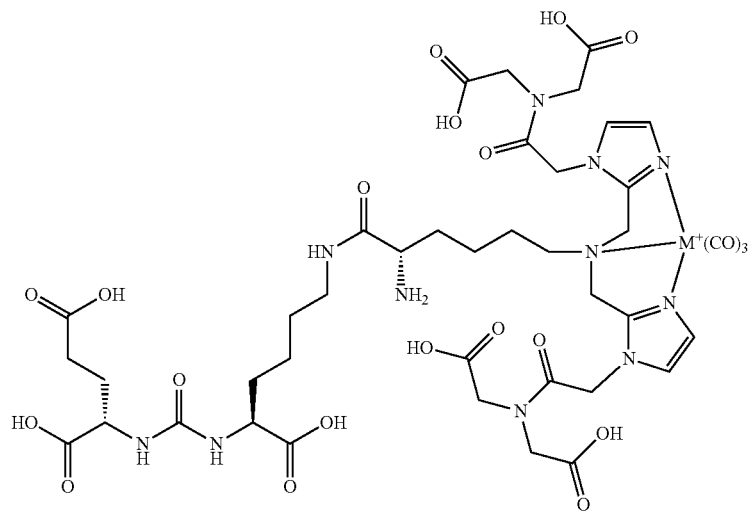

-continued
MIP-1404
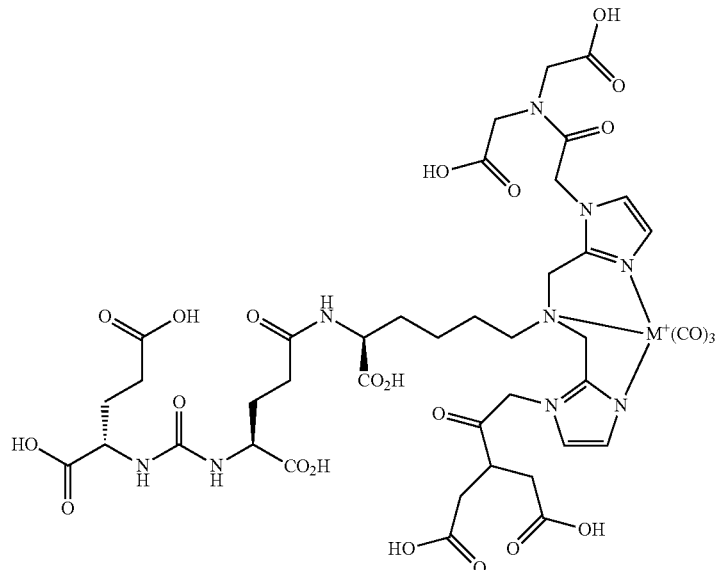
MIP-1405
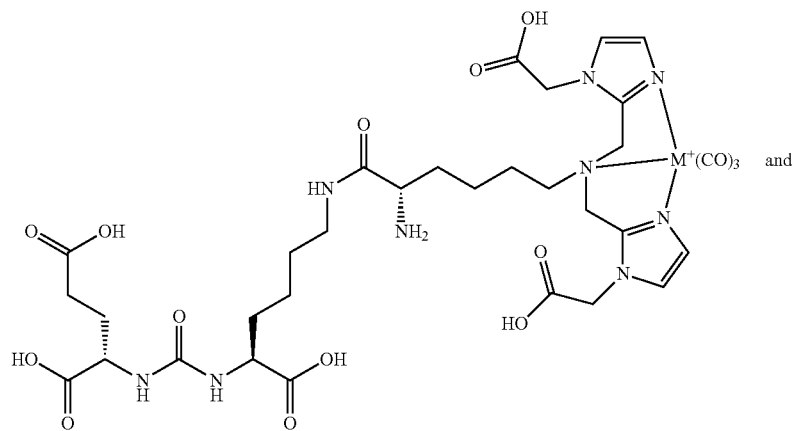
and
MIP-1379
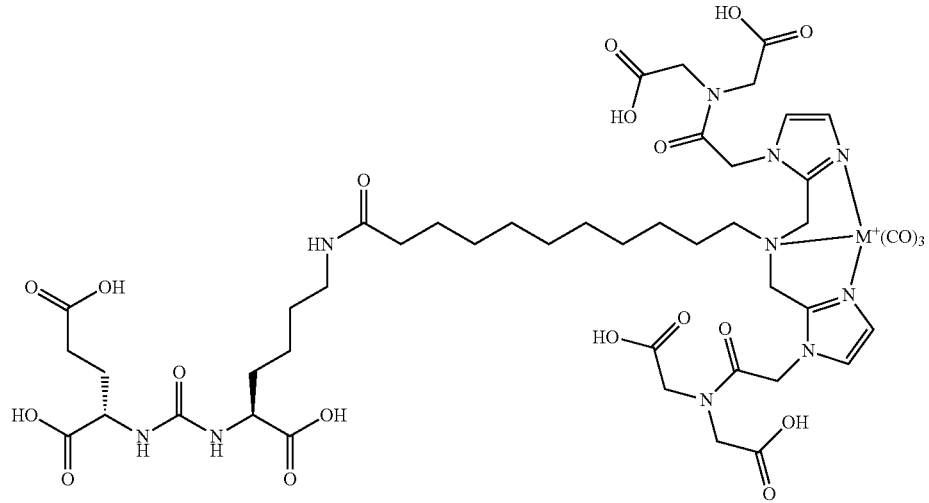

and M is absent or is a non-radionuclide metal and $^xI$ is a non-radionuclide of iodine.

7. The regimen of claim 1, wherein the compound is administered to the subject from about 0.2 mg/kg to about 100 mg/kg and the agent is administered to the subject from about 0.2 mg/kg to about 100 mg/kg.

8. A treatment protocol for a subject diagnosed with cancer, the protocol comprising:
   a) administering an agent to the subject;
   b) after allowing a waiting period of 1 hour to 60 hours to pass; and then
   c) administering a compound comprising a recognition moiety for Prostate Specific Membrane Antigen ("PSMA") and a radionuclide to the subject;
   wherein:
   the compound binds to both cancerous prostate tissue and non-cancerous tissue;
   the compound is administered in an amount sufficient to cause a displacement of the agent in cancerous tissue;
   the agent does not include a radionuclide;
   the compound is a Glu-urea-based PSMA ligand; and the agent comprises a Glu-urea-based PSMA ligand, a phosphinyl containing moiety, 7-(L-2-amino-2-carboxyethylthio)-2-(2,2-dimethyl cyclopropanecarboxamide)-2-heptenoic acid, 2-(phosphonomethyl)pentanedioic acid, or 2-(3-mercaptopropyl)pentanedioic acid (2-MPPA).

9. The treatment protocol of claim 8, wherein at least one of steps a) and c) are repeated at periodic intervals.

10. The treatment protocol of claim 8, wherein steps a), b), and c) are repeated.

11. The treatment protocol of claim 8 further comprising d) monitoring treatment by imaging using scintigraphy, single-photon emission computed tomography (SPECT), or positron emission tomography (PET).

12. The treatment protocol of claim 8, wherein the non-cancerous tissue is kidney tissue, salivary gland tissue, lacrimal gland tissue, parotid gland tissue, or small intestine tissue.

13. The treatment protocol of claim 8, wherein the radionuclide is a radioactive isotope of Ga, I, Y, Lu, Bi, Ac, Re, In, Th, or Tc.

14. The treatment protocol of claim 8, wherein the compound is:

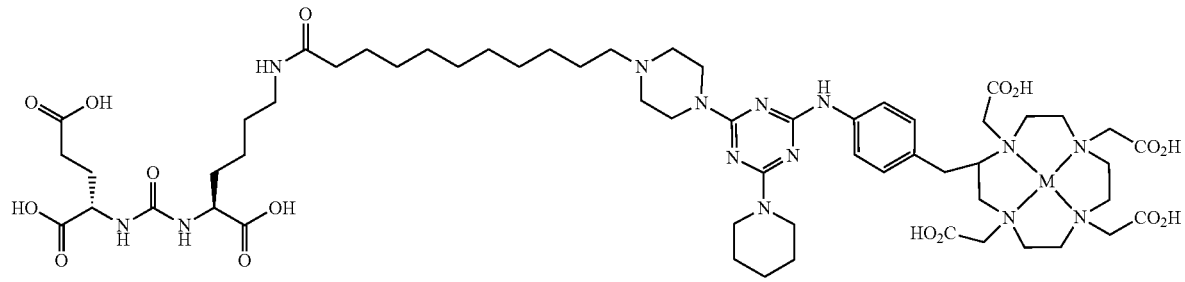

MIP-1555

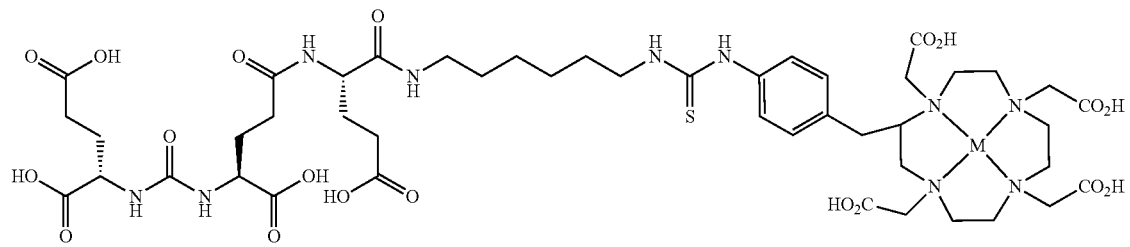

MIP-1519

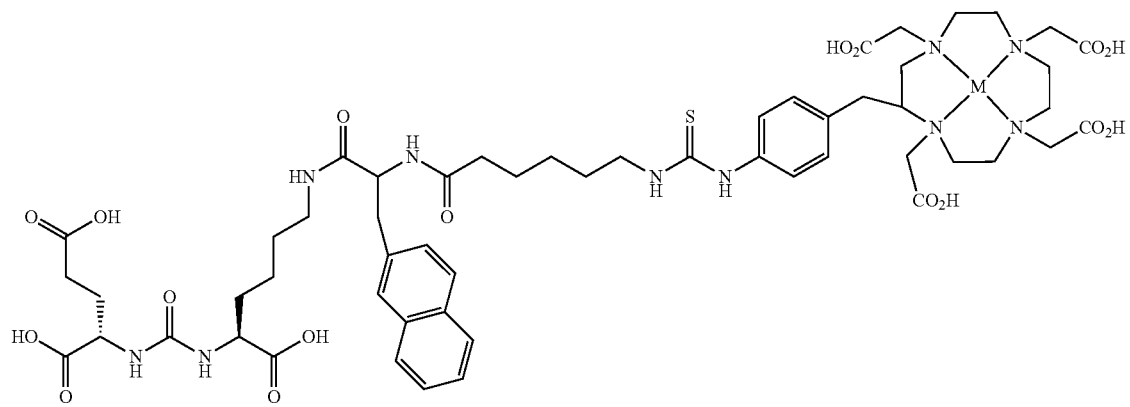

MIP-1545

-continued
MIP-1558
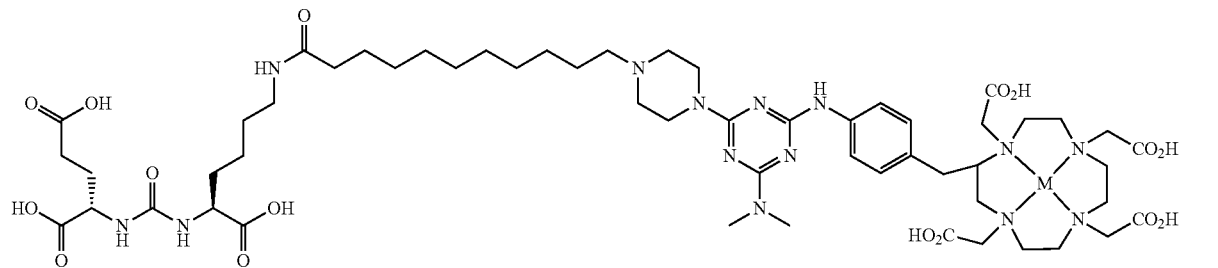
MIP-1072
MIP-1095
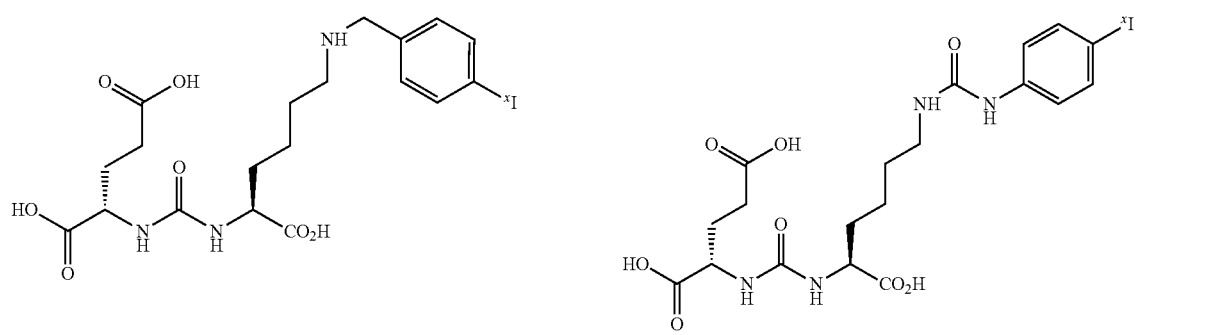
MIP-1427
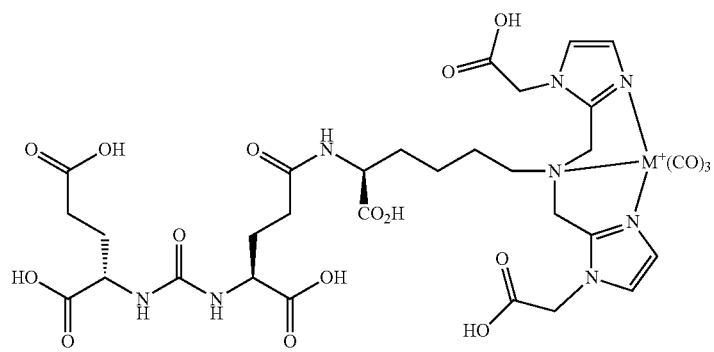
MIP-1428
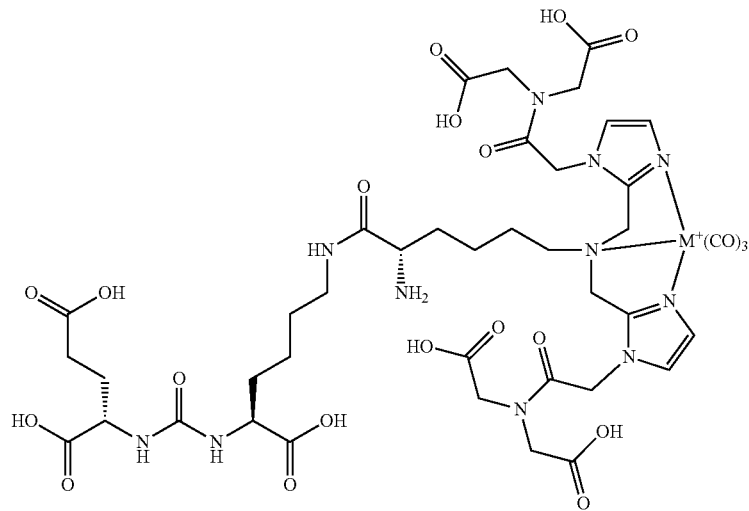

-continued

MIP-1404

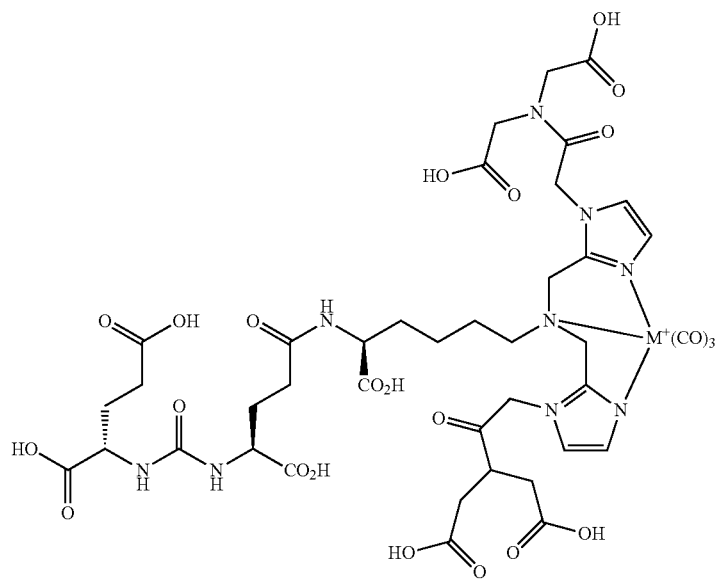

MIP-1405

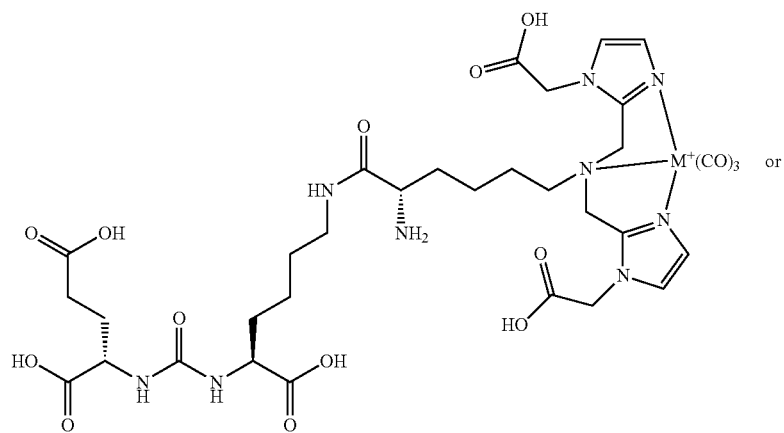

or

MIP-1379

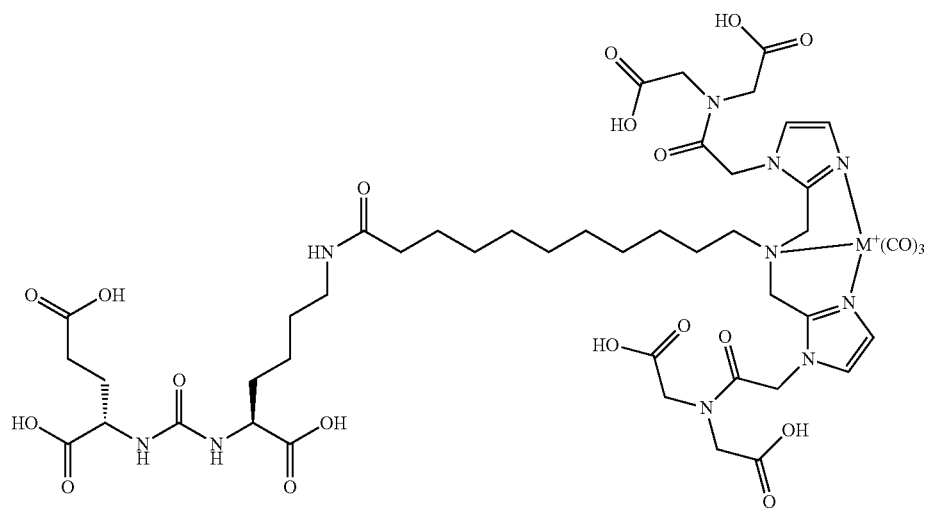

and wherein M is a radionuclide and $^xI$ is a radionuclide of iodine.

15. The treatment protocol of claim 8, wherein the agent comprises: 2-[[methylhydroxyphosphinyl]methyl]pentanedioic acid; 2-[[ethylhydroxyphosphinyl]methyl]pentanedioic acid; 2-[[propylhydroxyphosphinyl]methyl]pentanedioic acid; 2-[[butylhydroxyphosphinyl]methyl]pentanedioic acid; 2-[[cyclohexylhydroxyphosphinyl]methyl]pentanedioic acid; 2-[[phenylhydroxyphosphinyl]methyl]pentanedioic acid; 2-[[(phenylmethyl)

hydroxyphosphinyl]methyl]pentanedioic acid; 2-[[((2-phenylethyl)methyl)hydroxyphosphinyl]methyl]pentanedioic acid; 2-[[((3-phenylpropyl)methyl)hydroxyphosphinyl]methyl]pentanedioic acid; 2-[[((3-phenylbutyl)methyl)hydroxyphosphinyl]methyl]pentanedioic acid; 2-[[((2-phenylbutyl)methyl)hydroxyphosphinyl]methyl]pentanedioic acid; 2-[[(4-phenylbutyl)hydroxyphosphinyl]methyl]pentanedioic acid; 2-[[(aminomethyl)hydroxyphosphinyl]methyl]pentanedioic acid; 7-(L-2-amino-2-carboxyethylthio)-2-(2,2-dimethylcyclopropanecarboxamide)-2-heptenoic acid; 2-(phosphonomethyl)pentanedioic acid; N-[methylhydroxyphosphinyl]glutamic acid; N-[ethylhydroxyphosphinyl]glutamic acid; N-[propylhydroxyphosphinyl]glutamic acid; N-[butylhydroxyphosphinyl]glutamic acid; N-[phenylhydroxyphosphinyl]glutamic acid; N-[(phenylmethyl)hydroxyphosphinyl]glutamic acid; N-[((2-phenylethyl)methyl)hydroxyphosphinyl]glutamic acid; N-methyl-N-[phenylhydroxyphosphinyl]glutamic acid; 2-(3-mercaptopropyl)pentanedioic acid (2-MPPA), a pharmaceutically acceptable salt thereof; or a mixture of any two or more thereof.

16. The treatment protocol of claim 8, wherein the agent is a cold form of any one or more of:

MIP-1555

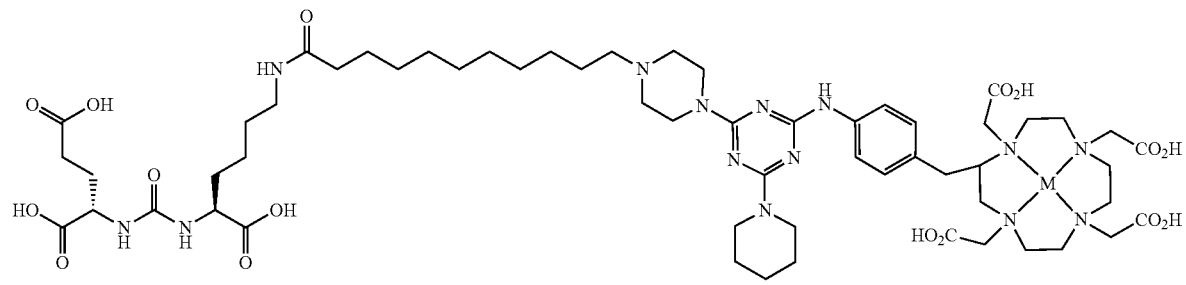

MIP-1519

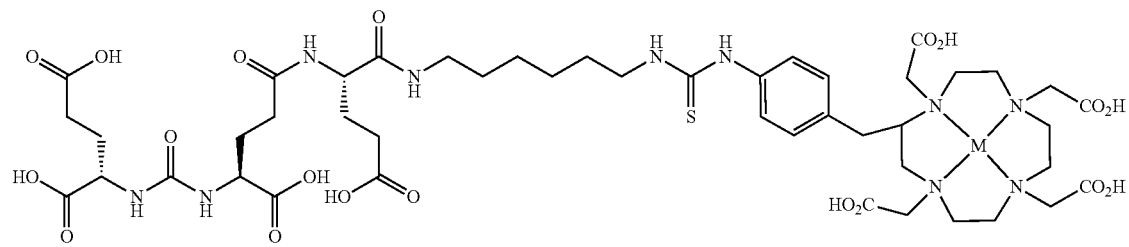

MIP-1545

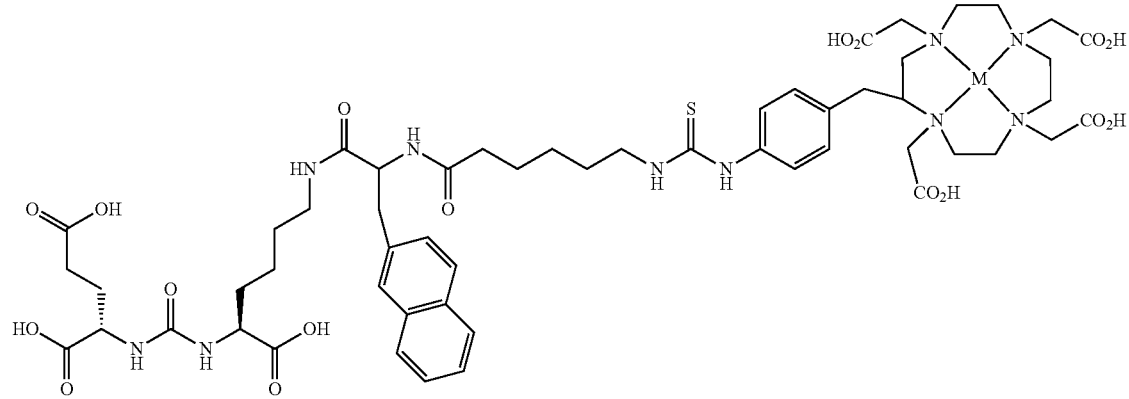

MIP-1558

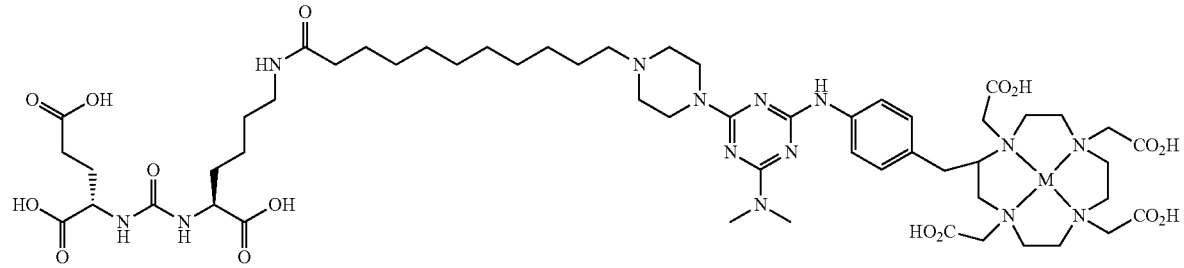

MIP-1072
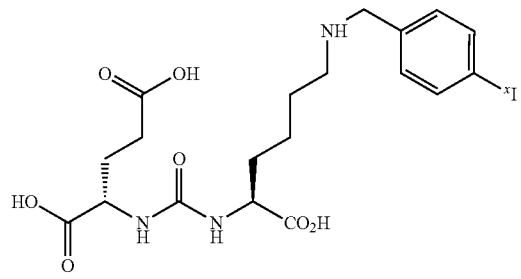
MIP-1095
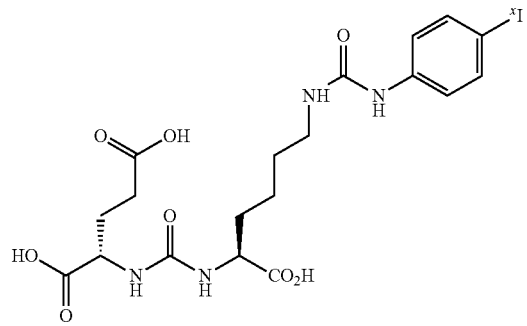
MIP-1427
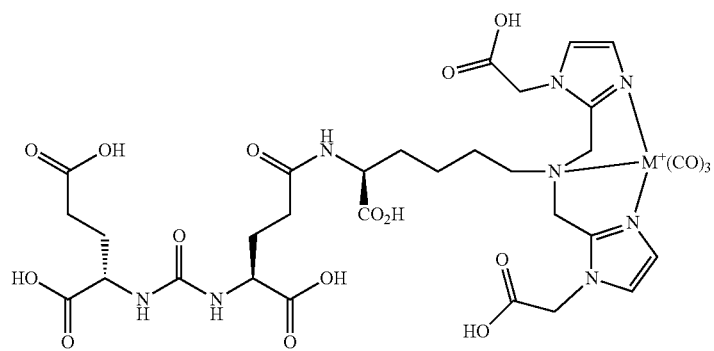
MIP-1428
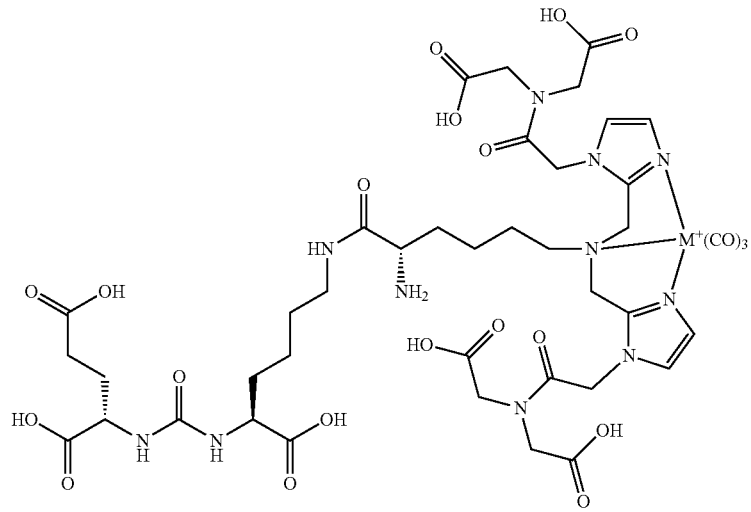

-continued
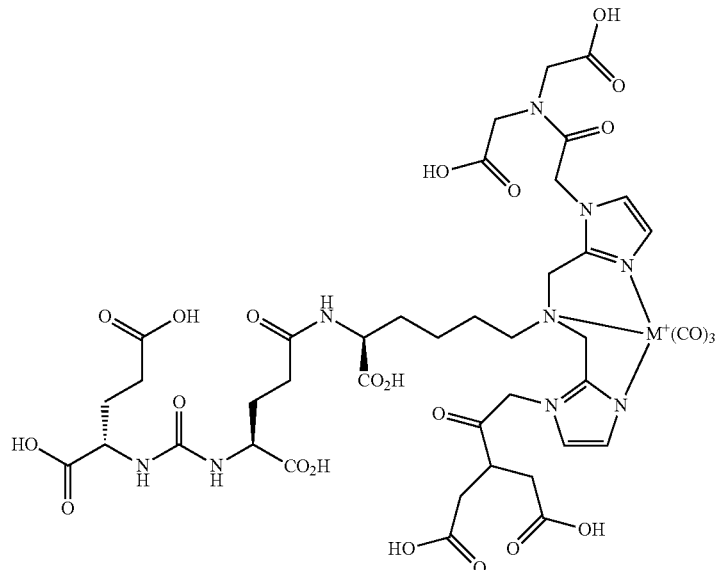
MIP-1404
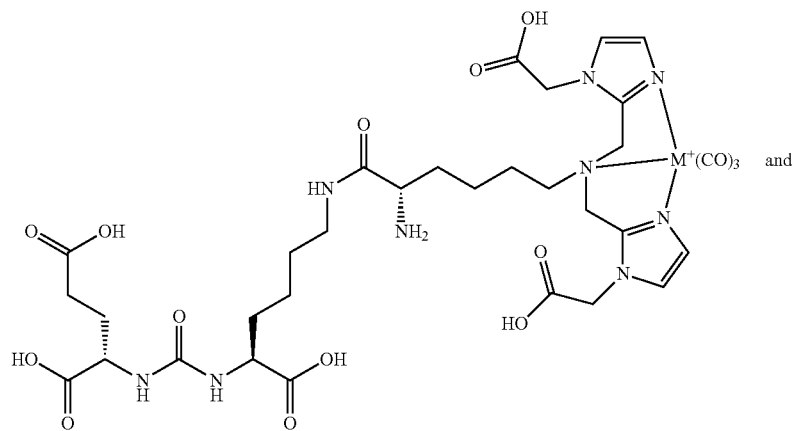
MIP-1405
and
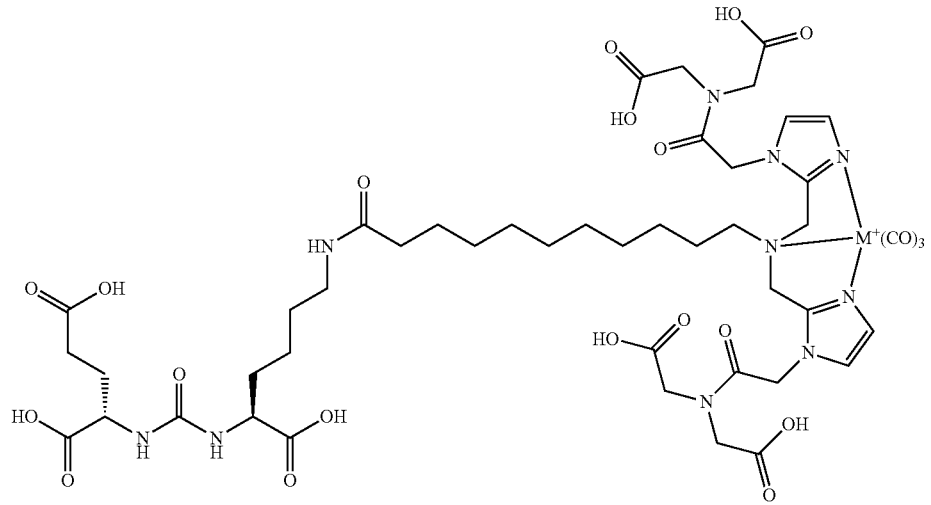
MIP-1379 and M is absent or is a non-radionuclide metal and $^x$I is a non-radionuclide of iodine.

17. The treatment protocol of claim 8, wherein the compound is administered to the subject from about 0.2 mg/kg to about 100 mg/kg, and the agent is administered to the subject from about 0.2 mg/kg to about 100 mg/kg.

\* \* \* \* \*